US012758446B2

(12) United States Patent
Sukumaran et al.

(10) Patent No.: US 12,758,446 B2
(45) Date of Patent: Oct. 13, 2026

(54) PATIENT SUPPORT APPARATUSES WITH LOCKING FEATURES

(71) Applicant: Stryker Corporation, Kalamazoo, MI (US)

(72) Inventors: Sujay Sukumaran, Portage, MI (US); Madhu Thomas, London (CA); Lavanya Vytla, McKinney, TX (US); Jason John Connell, London (CA); Jeremy L. Dunn, Portage, MI (US); Michael W. Graves, Paw Paw, MI (US); Matthew A. Cutler, Portage, MI (US); Donna-Marie Robertson, Portage, MI (US); Xianyu Shea, Vicksburg, MI (US); Berkay Güncan, Talas (TR); Mehmet Zihni Gurlek, Kayseri (TR); Paul Bradford, West Kirby (GB); Murat Serkan Kantarci, Kayseri (TR); Christian Fulljames, Grand Rapids, MI (US)

(73) Assignee: Stryker Corporation, Portage, MI (US)

( * ) Notice: Subject to any disclaimer, the term of this patent is extended or adjusted under 35 U.S.C. 154(b) by 117 days.

(21) Appl. No.: 18/724,936

(22) PCT Filed: May 19, 2023

(86) PCT No.: PCT/US2023/022817

§ 371 (c)(1),
(2) Date: Jun. 27, 2024

(87) PCT Pub. No.: WO2023/225246

PCT Pub. Date: Nov. 23, 2023

(65) Prior Publication Data

US 2025/0127670 A1 Apr. 24, 2025

Related U.S. Application Data

(60) Provisional application No. 63/417,516, filed on Oct. 19, 2022, provisional application No. 63/343,818, filed on May 19, 2022.

(51) Int. Cl.
*A61G 7/05* (2006.01)
*A61B 5/00* (2006.01)
(Continued)

(52) U.S. Cl.
CPC .......... *A61G 7/0524* (2016.11); *A61B 5/1115* (2013.01); *A61B 5/6892* (2013.01);
(Continued)

(58) Field of Classification Search
CPC .... A61G 7/0524; A61G 7/0509; A61G 7/015; A61G 7/018; G16H 50/30; A61B 5/1115; A61B 5/6892
(Continued)

(56) References Cited

U.S. PATENT DOCUMENTS 6,884,255 B1 4/2005 Newton
7,570,152 B2 8/2009 Smith et al.
(Continued)

FOREIGN PATENT DOCUMENTS

CA 3133535 A1 * 12/2020 ............... A61G 7/05
WO 2022056343 A1 3/2022

OTHER PUBLICATIONS

International Search Report and Written Opinion, PCT/US23/22817, dated Aug. 14, 2023, 27 pages.
(Continued)

*Primary Examiner* — Justin C Mikowski
*Assistant Examiner* — Deborah Talitha Gedeon
(74) *Attorney, Agent, or Firm* — Gardner, Linn, Burkhart & Ondersma LLP

(57) ABSTRACT

A patient support apparatus includes a frame, a support surface, a caregiver control panel, a patient control panel, and a controller. The caregiver control panel includes a lock out control that, when manually activated by a caregiver, locks out one or more particular controls on the patient
(Continued)

Auto-Lock control panel. The controller is also adapted to automatically lock out the one or more particular controls, irrespective of the state of the lock out control, in response to a triggering event. The triggering event may include one or more of the following: the arming of an exit detection system, the arming of a monitoring system, the passage of a predetermined time period, the use of a scale, the zeroing of the scale, the receipt of a fall risk score for the patient, etc. The caregiver control panel may allow the caregiver to select what patient controls are automatically locked out.

20 Claims, 10 Drawing Sheets

(51) Int. Cl.
*A61B 5/11* (2006.01)
*A61G 7/015* (2006.01)
*A61G 7/018* (2006.01)
*G16H 50/30* (2018.01)

(52) U.S. Cl.
CPC ............. *A61G 7/015* (2013.01); *A61G 7/018* (2013.01); *A61G 7/0509* (2016.11); *G16H 50/30* (2018.01)

(58) Field of Classification Search
USPC .............................................................. 5/616
See application file for complete search history.

(56) References Cited

U.S. PATENT DOCUMENTS 7,591,796 B1 9/2009 Barak et al.
8,334,779 B2 12/2012 Zerhusen et al.
8,756,078 B2 6/2014 Collins, Jr. et al.
9,204,823 B2 12/2015 Derenne et al.
9,230,421 B2 1/2016 Reeder et al.
9,642,759 B2 5/2017 Stryker et al.
9,934,427 B2 4/2018 Derenne et al.
10,130,536 B2 11/2018 Roussy et al.
10,403,401 B2 9/2019 Brosnan et al.
10,410,500 B2 9/2019 Derenne et al.
10,667,984 B2 6/2020 Brosnan et al.
11,141,334 B2 10/2021 Naber et al.
11,337,872 B2 5/2022 Bhimavarapu et al.
11,382,813 B2 7/2022 Moreno et al.
11,786,426 B2 10/2023 Murai
2008/0172789 A1* 7/2008 Elliot .................. A61G 7/0527 5/616
2012/0073054 A1 3/2012 O'Keefe et al.
2014/0297327 A1 10/2014 Heil et al.
2015/0095241 A1 4/2015 Edwards
2016/0287215 A1* 10/2016 Choi .................... A61B 8/5207
2016/0349854 A1* 12/2016 Hayes ..................... G06F 3/016
2017/0143566 A1 5/2017 Elku et al.
2018/0185222 A1 7/2018 Zerhusen et al.
2020/0046586 A1* 2/2020 Furman .................. A61G 7/005
2020/0197247 A1* 6/2020 Nahavandi ............. G16H 40/63
2020/0294674 A1* 9/2020 Emmons .............. A61B 5/0205
2020/0375828 A1 12/2020 Wiggermann et al.
2021/0045950 A1 2/2021 Connell et al.
2022/0122724 A1 4/2022 Durlach et al.

OTHER PUBLICATIONS

CHG Hospital Beds, The Spirit Bed, Ref 1-70-001, User Manual for Spirit Beds, dated Pre-2014.
Stryker, EPIC & EPIC+ Critical Care Bed, Model 2030/2031, Maintenance Manual, dated Oct. 2000.
Stryker, InTouch Critical Care Bed, Model FL27 (2131/2141), Maintenance Manual, dated Sep. 2008.
Stryker, Modular Patient System (MPS) 3000 Bed, Maintenance Manual, dated Mar. 1994.
Stryker, S3 MedSurg Bed with StayPut Frame, REF 3005, Maintenance Manual, dated Jun. 2016.
Stryker, ProCuity Bed Series, REF 300900002, Maintenance Manual, dated Mar. 2021.
Stryker, MV3 Bariatric Bed, REF 5900, Maintenance Manual, dated Sep. 2020.

* cited by examiner

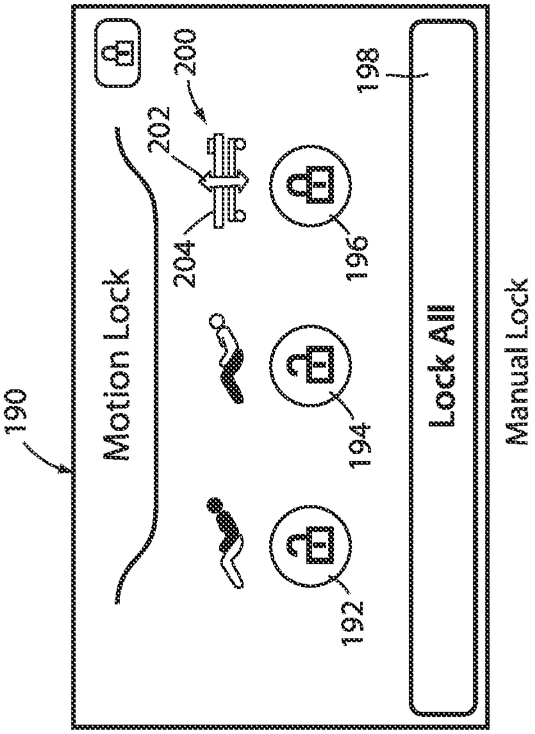
Manual Lock
FIG. 12
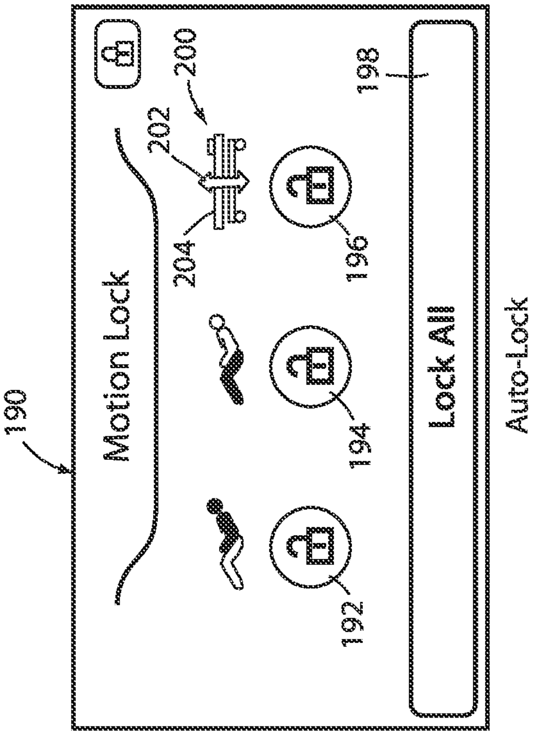
Auto-Lock
FIG. 13
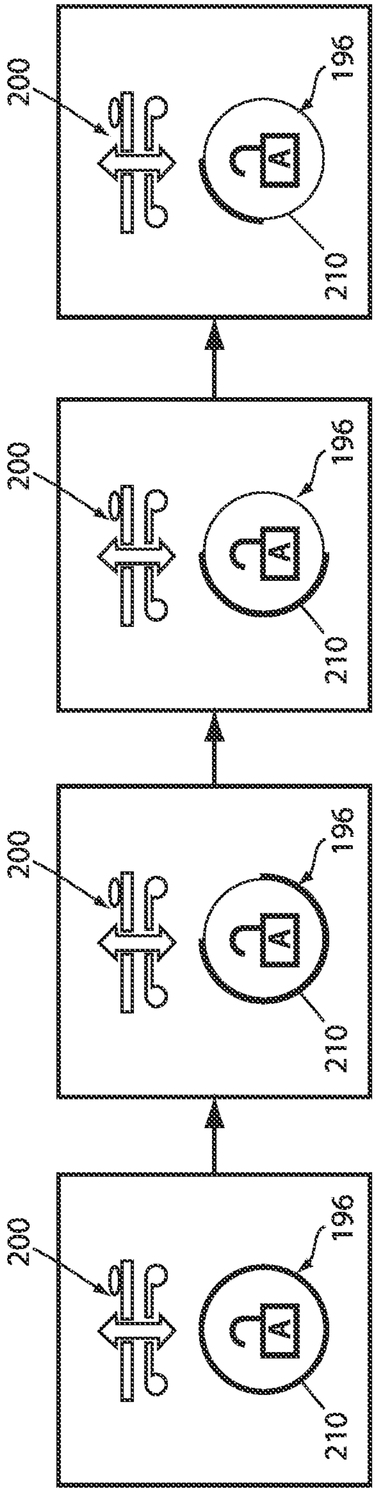
FIG. 14A
FIG. 14B
FIG. 14C
FIG. 14D

PATIENT SUPPORT APPARATUSES WITH LOCKING FEATURES

BACKGROUND

The present disclosure relates to patient support apparatuses, such as beds, cots, stretchers, recliners, or the like. More specifically, the present disclosure relates to patient support apparatuses that include one or more lock out features for preventing a patient from using certain functions of the patient support apparatus.

Existing hospital beds often include a patient control panel that includes a plurality of buttons or other types of controls. The patient control panel typically includes controls that allow the patient to move one or more components of the patient support apparatus, such as pivoting the Fowler section, changing the angle of a knee section, and/or changing the overall height of the support surface on which the patient is positioned. In some situations, it is desirable for the caregiver to disable (i.e. lock out) one or more of these controls in order to prevent the patient from moving one or more components of the patient support apparatus. The caregiver may desire to lock out these controls in order to reduce the risk of injury that might otherwise occur if the controls were not locked out, and/or because the caregiver has configured the patient support apparatus in a desired physical configuration and doesn't want the patient to change that configuration.

SUMMARY

According to various embodiments, the present disclosure provides a patient support apparatus with one or more improved lock out features. These features include, but are not limited to, the automatic locking out of certain patient controls when a triggering event is detected, the automatic cessation of the lock outs when the triggering event terminates, the inclusion of manual lock out controls that work in conjunction with the automatic lock outs, the customization of the automatic lock outs, and the notification to the user of which type of lock out (manual, automatic, or both) is currently active. These and other aspects of the present disclosure will be apparent to a person skilled in the art in light of the accompanying drawings and the following written description.

According to a first aspect of the present disclosure, a patient support apparatus is provided that includes a base, a plurality of lifts, a frame, a support surface, a patient control panel, a caregiver control panel, and a controller. The frame is supported on the lifts and the lifts are adapted to change a height of the frame. The support surface is supported on the frame. The caregiver control panel includes a lockout control adapted to be activated by a caregiver, and the patient control panel includes a first control adapted to be activated by the patient. The controller is adapted to move a first component of the patient support apparatus when the first control is activated and the lockout control is not activated, to lock out operation of the first control in response to the lockout control being manually activated, and to automatically lock out operation of the first control when the controller detects a triggering event regardless of whether the lockout control is manually activated or not.

According to another aspect of the present disclosure, a patient support apparatus is provided that includes a base, a plurality of lifts, a frame, a support surface, a patient control panel, a caregiver control panel, and a controller. The frame is supported on the lifts and the lifts are adapted to change a height of the frame. The support surface is supported on the frame. The caregiver control panel includes a lockout control adapted to be activated by a caregiver, and the patient control panel includes a first control adapted to be activated by the patient. The controller is adapted to automatically lock out operation of the first control in response to a triggering event, to display a first lockout indication for the first control when the lockout control is manually activated by the caregiver, to display a second lockout indication for the first control when the lockout is automatically locked out in response to the triggering event, and to display neither the first nor second lockout indication when the lockout control is not manually activated by the caregiver and the triggering event is absent.

According to still another aspect of the present disclosure, a patient support apparatus is provided that includes a base, a plurality of lifts, a frame, a support surface, a display, a patient control panel, and a controller. The frame is supported on the lifts and the lifts are adapted to change a height of the frame. The support surface is supported on the frame. The patient control panel includes a set of controls adapted to be activated by the patient. The controller is adapted to display an automatic lockout control screen on the display that is adapted to allow the caregiver to select a subset of the set of controls. The controller is further adapted to automatically lock out the selected controls in response to a triggering event.

According to yet another aspect of the present disclosure, a patient support apparatus is provided that includes a base, a plurality of lifts, a frame, a support surface, a caregiver control panel, a patient control panel, and a controller. The frame is supported on the lifts and the lifts are adapted to change a height of the frame. The support surface is supported on the frame. The patient control panel includes a plurality of patient controls adapted to be activated by a patient. The caregiver control panel includes a plurality of caregiver controls adapted to be activated by a caregiver. The controller is adapted to automatically lock out operation of a first set of controls when the controller detects a first triggering event and to automatically lock out operation of a second set of controls different than the first set of controls when the controller detects a second triggering event different from the first triggering event.

According to other aspects of the present disclosure, the first set of controls may include at least one control from the plurality of patient controls.

In some aspects, the second set of controls may include at least one control from the plurality of caregiver controls.

The caregiver control panel, in some aspects, is adapted to allow a caregiver to override the automatic lock out of both the first set of controls and the second set of controls.

According to still other aspects of the present disclosure, the first control is a height control adapted to raise a height of the frame when the height control is activated and the lockout control is not activated.

In some aspects of the present disclosure, the caregiver control panel is adapted to enter a sleep mode after a predetermined time period elapses without the caregiver using the caregiver control panel, and the triggering event is the caregiver control panel entering the sleep mode.

The controller, in some aspects, is further adapted to receive a fall risk score of the patient, and to use the receipt of the fall risk score as the triggering event if the fall risk score exceeds a threshold level.

The patient support apparatus, in some aspects, further includes a network transceiver adapted to communicate with a local area network of a healthcare facility. In such aspects, the controller may further be adapted to receive the fall risk score from an electronic medical records server accessible through the local area network.

Alternatively, or additionally, the controller may be adapted to allow a caregiver to communicate the patient's fall risk score to the controller using the caregiver control panel.

In some aspects, the patient support apparatus includes an exit detection system adapted to be armed and disarmed and to operate with a plurality of different sensitivity levels when armed. The exit detection system is adapted to issue an alert when the exit detection system is armed and a patient exits from the patient support apparatus. The triggering event may be the arming of the exit detection system at a first one of the plurality of sensitivity levels but not at a second one of the plurality of sensitivity levels.

In some aspects, the patient support apparatus further includes a plurality of wheels coupled to the base, a brake adapted to selectively brake and unbrake at least one of the plurality of wheels, a plurality of siderails adapted to be moved between raised and lowered positions, and a monitoring system adapted to be armed and disarmed. When armed, the monitoring system is adapted to monitor a first state of the brake and a second state of the siderails and to issue an alert if any one of the first or second states changes to an undesired state. The triggering event may be the arming of the monitoring system.

The monitoring system, in some aspects, may also be adapted to monitor, when armed, a height of the frame.

In some aspects, the monitoring system may also be adapted to monitor whether the exit detection system is armed or disarmed.

The patient support apparatus, in some aspects, further includes a scale system and a scale control. The scale system is adapted to detect a weight of the patient and the scale control is positioned on the caregiver control panel. The controller is adapted to record the weight of the patient in response to activation of the scale control and the triggering event is the activation of the scale control.

In some aspects, the caregiver control panel includes a scale zeroing control and the controller is adapted to tare the scale system in response to activation of the scale zeroing control. The triggering event may be the activation of the scale zeroing control.

The controller, in some aspects, is adapted to automatically and repetitively take weight readings from the scale system to determine if the patient is occupying the patient support apparatus or not. The triggering event may be the absence of the patient from the patient support apparatus.

In some aspects, the lifts are adapted to tilt the frame and the support surface includes a section adapted to pivot. The caregiver control panel may include a configuration control that, when activated, causes the controller to tilt the frame and pivot the section to a particular configuration when the configuration control is activated. The triggering event may be the activation of the configuration control.

The configuration control, in some aspects, is adapted to tilt the frame and pivot the section to one of the following configurations: (a) a Trendelenburg configuration, (b) a reverse Trendelenburg configuration, (c) an examination configuration, or (d) a vascular configuration.

In some aspects, the triggering event is a current height of the litter frame exceeding a threshold height.

In some aspects, the triggering event is a passage of a predetermined amount of time after movement of a component of the patient support apparatus ceases.

In some aspects, the triggering event is the arming of the exit detection system.

In some aspects, the triggering event is the detection of the patient, and/or the patient's center of gravity, at a perimeter location on the litter frame of the patient support apparatus.

In some aspects, the controller is adapted to automatically lock out a control adapted to deactivate a brake in response to the detection of the triggering event.

The caregiver control panel, in some aspects, includes a second height control adapted to be activated by a caregiver, and the controller is adapted to raise a height of the frame when the second height control is activated and the lockout control is not activated. The controller is further adapted to not automatically lock out operation of the second height control when the controller detects the triggering event.

In some aspects, the patient control panel further includes a motion control, and the controller is adapted to move a component of the patient support apparatus in response to activation of the motion control when the motion control is not locked out. The controller is also adapted to automatically lock out operation of the motion control when the controller detects the triggering event.

The patient control panel, in some aspects, includes a second control, and the caregiver control panel is adapted to allow a caregiver to select or deselect an auto-locking function for the second control. The controller is adapted to automatically lock out operation of the second control when the triggering event is detected and the auto-locking function is selected, and to not automatically lock out operation of the second control when the triggering event is detected and the auto-locking function is deselected.

In some aspects, the second control is adapted to raise a pivotable section of the support surface.

The patient support apparatus, in some aspects, further includes a plurality of siderails positioned alongside the support surface. Each of the siderails includes an outer surface facing away from the support surface and an inner surface facing toward the support surface. The patient control panel may be positioned on one of the inner surfaces of the siderails and the caregiver control panel may be positioned on one of the outer surfaces of the siderails.

The patient support apparatus, in some aspects, further includes a second patient control panel that includes a second height control adapted to be activated by the patient. The controller is further adapted to raise the height of the frame when the second height control is activated and the lockout control is not activated, and to automatically lock out operation of the second height control when the controller detects the triggering event regardless of whether the lockout control is manually activated or not.

The patient control panel, in some aspects, is adapted to display a first lockout indication when the lockout control is manually activated by the caregiver and to display a second lockout indication when the controller automatically locks out operation of the height control. The first indication is different from the second indication.

In some aspects, the first control includes a first icon and the first indication includes illuminating the first icon in a first manner and the second indication includes illuminating the first icon in a second manner different from the first manner.

In some aspects, the second manner includes adding a letter "A" to the first icon.

The controller, in some aspects, is adapted to automatically cancel the automatic lock out in response to an absence of the triggering event.

In some aspects, the subset of controls includes a first control and a second control and the first control and second control are each adapted to perform one of the following: (1) change an orientation of a pivotable head section of support surface; (2) change an orientation of a pivotable knee section of the support surface; or (3) change a height of the frame.

In some aspects, the subset of controls includes a height control adapted to raise a height of the frame when the height control is activated and the controller has not automatically locked out the height control.

Before the disclosure is explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 12 is an illustrative motion lock screen that may be displayed on the display of the patient support apparatus and that includes an illustrative indication of a manually activated lock out;

FIG. 13 is the motion lock screen of FIG. 12 shown in a state that includes an illustrative indication of an automatically activated lock out;

FIG. 14*a* illustrates a first state of an auto-lock timer;

FIG. 14*b* illustrates a second state of the auto-lock timer of FIG. 14*a;*

FIG. 14*c* illustrates a third state of the auto-lock timer of FIG. 14*a;*

FIG. 14*d* illustrate a fourth state of the auto-lock timer of FIG. 14*a*.

DETAILED DESCRIPTION OF THE EMBODIMENTS

Figure 1:
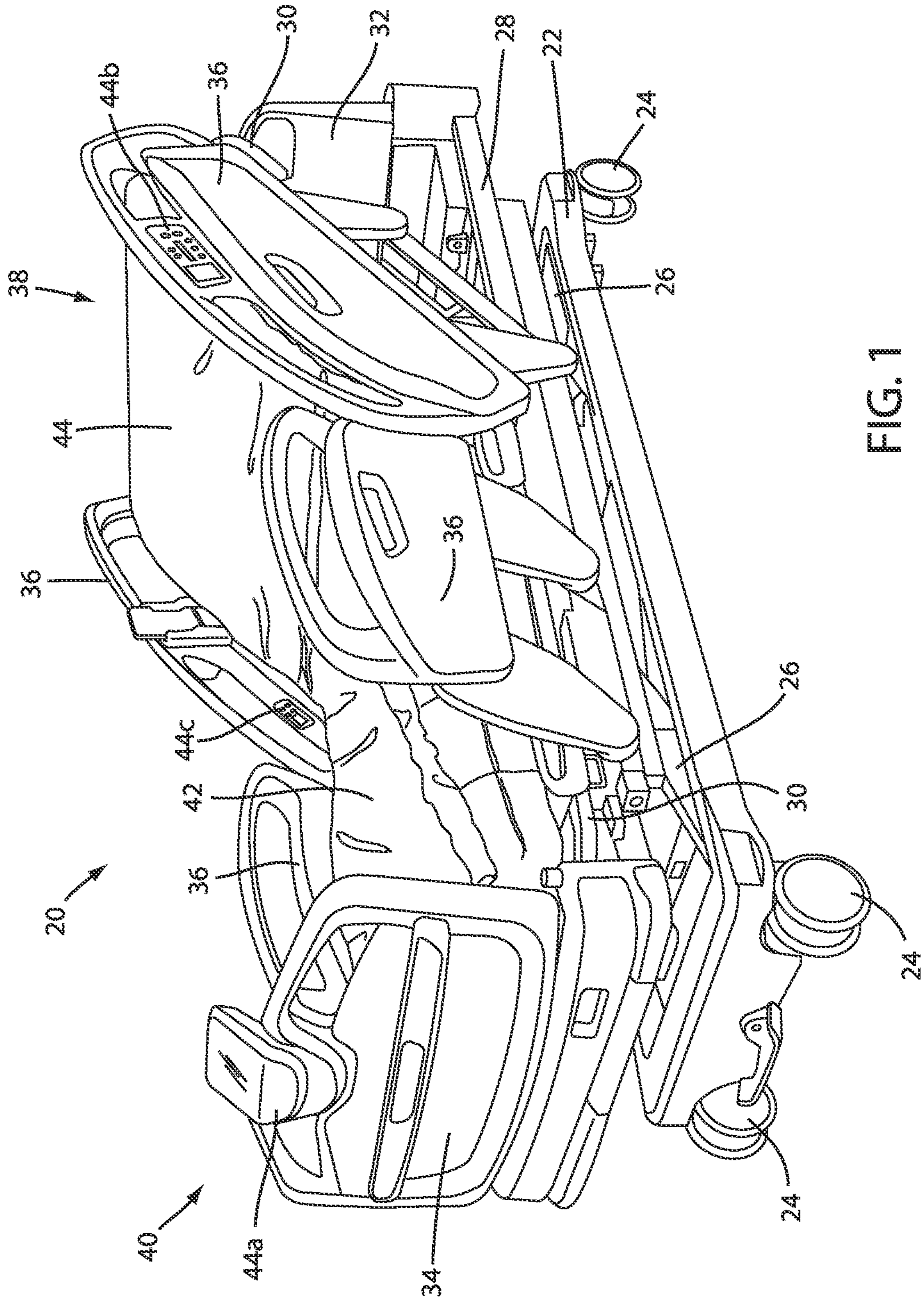
FIG. 1 is a perspective view of a patient support apparatus according to a first embodiment of the present disclosure.

An illustrative patient support apparatus 20 according to an aspect of the present disclosure are shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, or any other structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a headboard 32, a footboard 34 and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted, to place the litter frame 28 in a flat or horizontal orientation, a Trendelenburg orientation, or a reverse Trendelenburg orientation. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard 32, footboard 34, and siderails 36. Support deck 30 provides a support surface for a mattress 42, or other soft cushion, so that a person may lie and/or sit thereon. In some embodiments, the mattress 42 includes one or more inflatable bladders that are controllable via a blower, or other source of pressurized air. In at least one embodiment, the inflation of the bladders of the mattress 42 is controllable via electronics built into patient support apparatus 20. In one such embodiments, mattress 42 may take on any of the functions and/or structures of any of the mattresses disclosed in commonly assigned U.S. Pat. No. 9,468,307 issued Oct. 18, 2016, to inventors Patrick Lafleche et al., the complete disclosure of which is incorporated herein by reference. Still other types of mattresses may be used.

Support deck 30 is made of a plurality of sections, some of which are pivotable about generally horizontal pivot axes. In the embodiment shown in FIG. 1, support deck 30 includes at least a head section, a thigh section, and a foot section, all of which are positioned underneath mattress 42 and which generally form flat surfaces for supporting mattress 42. The head section, which is also sometimes referred to as a Fowler section, is pivotable about a generally horizontal pivot axis between a generally horizontal orientation (not shown) and a plurality of raised positions (one of which is shown in FIG. 1). The thigh section and foot section may also be pivotable about generally horizontal pivot axes. Such pivoting occurs at the junction of the thigh and foot section so as to raise or lower the patient's knees. This pivoting is sometimes referred to as a gatch mechanism.

In some embodiments, patient support apparatus 20 may be modified from what is shown to include one or more components adapted to allow the user to extend the width of patient support deck 30, thereby allowing patient support apparatus 20 to accommodate patients of varying sizes. When so modified, the width of deck 30 may be adjusted sideways in any increments, for example between a first or minimum width, a second or intermediate width, and a third or expanded/maximum width.

It will be understood by those skilled in the art that patient support apparatus 20 can be designed with other types of mechanical constructions that are different from what is shown in the attached drawings, such as, but not limited to, the construction described in commonly assigned, U.S. Pat. No. 10,130,536 to Roussy et al., entitled PATIENT SUPPORT USABLE WITH BARIATRIC PATIENTS, the complete disclosure of which is incorporated herein by reference. In another embodiment, the mechanical construction of patient support apparatus 20 may include the same, or nearly the same, structures as the Model 3002 S3 bed manufactured and sold by Stryker Corporation of Kalamazoo, Michigan. This construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. In still another embodiment, the mechanical construction of patient support apparatus 20 may include the same, or nearly the same, structure as the Model 3009 Procuity MedSurg bed manufactured and sold by Stryker Corporation of Kalamazoo, Michigan. This construction is described in greater detail in the Stryker Maintenance Manual for the 3009 Procuity MedSurg bed (publication 3009-009-002, Rev. A.0), published in 2020 by Stryker Corporation of Kalamazoo, Michigan.

It will be understood by those skilled in the art that patient support apparatus 20 can be designed with still other types of mechanical constructions, such as, but not limited to, those described in commonly assigned, U.S. Pat. No. 769, 059 issued Apr. 6, 2010, to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The overall mechanical construction of patient support apparatus 20 may also take on still other forms different from what is disclosed in the aforementioned references provided the patient support apparatus includes one or more of the functions, features, and/or structures discussed in greater detail below.

Patient support apparatus 20 further includes a plurality of control panels 44 that enable a user of patient support apparatus 20, such as a patient and/or an associated caregiver, to control one or more aspects of patient support apparatus 20. In the embodiment shown in FIG. 1, patient support apparatus 20 includes a footboard control panel **44*a*, a pair of outer siderail control panels 44*b* (only one of which is visible), and a pair of inner siderail control panels 44*c* (only one of which is visible). Footboard control panel 44*a* and outer siderail control panels 44*b* are intended to be used by caregivers and will be referred to herein as caregiver control panels 44*a* and 44*b*. Inner siderail control panels 44*c* are intended to be used by the patient associated with patient support apparatus 20 and will be referred to herein as patient control panels 44*c*. Each of the control panels 44 includes a plurality of controls 50 (see, e.g. FIGS. 2, 4-5), although each control panel 44** does not necessarily include the same controls and/or functionality.

Among other functions, controls 50 of control panel **44*a* allow a user to control one or more of the following: change a height of support deck 30, raise or lower the Fowler section, activate and deactivate a brake for wheels 24, change the configuration of litter frame 28 and support deck 30, take patient weight readings using an onboard scale system, arm and disarm an exit detection system 48 (FIG. 4), change various settings on patient support apparatus 20, and perform other actions. One or both of the patient control panels 44*c*** may also include at least one control that enables a patient to call a remotely located nurse (or other caregiver).

Figure 4:
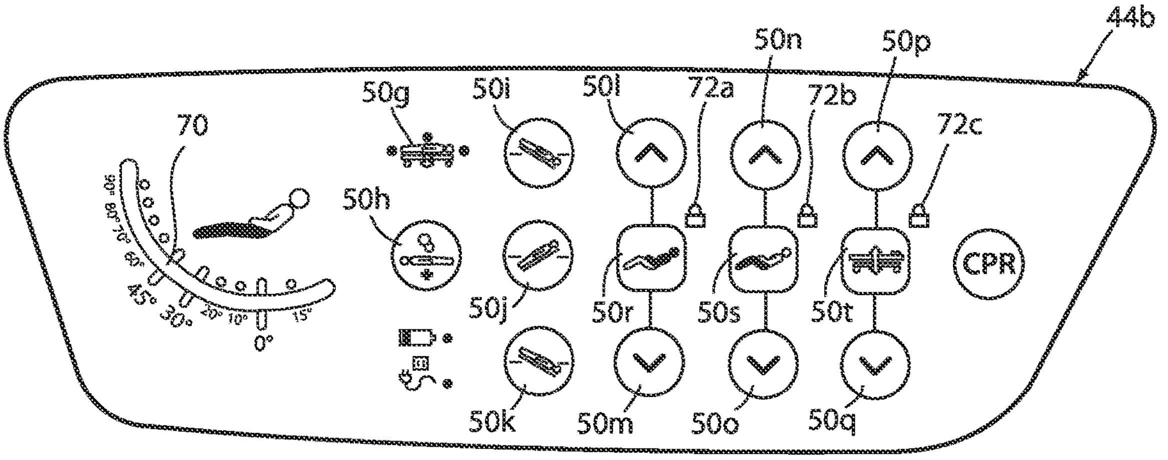
FIG. 4 is a plan view of a second illustrative caregiver control panel of the patient support apparatus.

Caregiver control panel **44*a* includes a display 52 (FIG. 2) configured to display a plurality of different screens thereon. Surrounding display 52 are a plurality of navigation controls 50*a-f* that, when activated, cause the display 52 to display different screens on display 52. More specifically, when a user presses navigation control 50*a*, control panel 44*a* displays an exit detection control screen on display 52 that includes one or more icons that, when touched, control the onboard exit detection system 48 (FIG. 4). One example of such an exit detection control screen is shown herein in FIG. 6. The exit detection system 48 is as adapted to issue an alert when a patient exits from patient support apparatus 20. Exit detection system 48 may include any of the same features and functions as, and/or may be constructed in any of the same manners as, the exit detection system disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference. Other types of exit detection systems may be included within patient support apparatus 20**.

When a user presses navigation control **50*b* (FIG. 2), control panel 44 displays a monitoring control screen on display 52 that includes a plurality of control icons that, when touched, control an onboard monitoring system 54 built into patient support apparatus 20. The onboard monitoring system alerts the caregiver through a unified indicator, such as a light or a plurality of lights controlled in a unified manner, when any one or more of a plurality of settings on patient support apparatus 20 are in an undesired state, and uses that same unified indicator to indicate when all of the plurality of settings are in their respective desired states. Further details of one type of monitoring system that may be built into patient support apparatus 20 are disclosed in commonly assigned U.S. patent application Ser. No. 62/864,638 filed Jun. 21, 2019, by inventors Kurosh Nahavandi et al. and entitled PATIENT SUPPORT APPARATUS WITH CAREGIVER REMINDERS, as well as commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference. Other types of monitoring systems may be included within patient support apparatus 20**.

When a user presses navigation control 50*c*, control panel 44*a* displays a scale control screen on display 52 that includes a plurality of control icons that, when touched, control a scale system 56 of patient support apparatus 20. One example of a scale control screen is shown herein in FIG. 7. Scale system 56 may include any of the same features and functions as, and/or may be constructed in any of the same manners as, the scale systems disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, and U.S. patent application Ser. No. 62/885,954 filed Aug. 13, 2019, by inventors Kurosh Nahavandi et al. and entitled PATIENT SUPPORT APPARATUS WITH EQUIPMENT WEIGHT LOG, the complete disclosures of both of which are incorporated herein by reference. The scale system 56 may utilize the same force sensors that are utilized by the exit detection system 48, or it may utilize one or more different sensors. Scale system 56 may also, in some embodiments, utilize a common microprocessor and/or other components that are also utilized by exit detection system 48. Other scale systems besides those mentioned above in the '254 and '954 applications may alternatively be included within patient support apparatus 20.

When a user presses navigation control 50*d*, control panel 44 displays a motion control screen on display 52 that includes a plurality of control icons that, when touched, control the movement of various components of patient support apparatus 20, such as, but not limited to, the height of litter frame 28 and the pivoting of the Fowler section. In some embodiments, the motion control screen displayed on display 52 in response to pressing control 50*d* may be the same as, or similar to, the position control screen 216 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference. Other types of motion control screens may be included on patient support apparatus 20.

When a user presses navigation control 50*e*, control panel 44*a* displays a motion lock control screen that includes a plurality of control icons that, when touched, control one or more manually-activated motion lockout functions of patient support apparatus 20. Such motion lockout functions typically include the ability for a caregiver to use control panel 44*a* to manually lock out one or more of the motion controls 50 of the patient control panels 44*c* such that the patient is not able to use those controls 50 on control panels 44*c* to control the movement of one or more components of patient support apparatus 20. Two examples of a motion lockout screen are shown herein in FIGS. 12 and 13. Other types of motion lockout screens may be used, and such lockout screens may include any of the features and functions as, and/or may be constructed in any of the same manners as, the motion lockout features, functions, and constructions disclosed in commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosure of which is incorporated herein by reference. Other types of motion lockout screens may be included within patient support apparatus 20.

When a user presses on navigation control 50*f*, control panel 44*a* displays a menu screen that includes a plurality of menu icons that, when touched, bring up one or more additional screens for controlling and/or viewing one or more other aspects of patient support apparatus 20. Such other aspects include, but are not limited to, diagnostic and/or service information for patient support apparatus 20, mattress control and/or status information, configuration settings, location information, automatic lockout settings, and other settings and/or information. One example of a menu screen is shown herein in FIG. 9. Another type of suitable of menu screen includes, but is not limited to, the menu screen 100 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference. Still other types of menus and/or settings may be included within patient support apparatus 20.

In at least one embodiment, utilization of navigation control 50*f* allows a user to navigate to a screen that enables a user to see which medical devices, if any, are currently associated with patient support apparatus 20. In some embodiments, patient support apparatus 20 is configured to automatically associate one or more devices with itself when those devices meet certain association conditions, such as being located within a predefined volume of space that encompasses and surrounds patient support apparatus 20. In such embodiments, patient support apparatus 20 includes an onboard locating system that is adapted to automatically determine the relative position of one or more devices with respect to patient support apparatus 20 and, in some instances, automatically associate those devices with patient support apparatus 20 (and/or the patient assigned to patient support apparatus 20) depending upon the proximity of the medical device to patient support apparatus 20 and/or other criteria. Further details of such a locating system and association process are disclosed in commonly assigned U.S. patent application Ser. No. 63/314,221 filed Feb. 25, 2022, by inventors Jerald Trepanier et al. and entitled COMMUNICATION SYSTEM FOR PATIENT SUPPORT APPARATUSES AND TEMPERATURE MANAGEMENT DEVICES, the complete disclosure of which is incorporated herein by reference.

For all of the navigation controls 50*a-f* (FIG. 2), screens other than the ones specifically mentioned above may be displayed on display 52 in other embodiments of patient support apparatus 20 in response to a user pressing these controls. Thus, it will be understood that the specific screens mentioned above are merely representative of the types of screens that are displayable on display 52 in response to a user pressing on one or more of navigation controls 50*a-f*. It will also be understood that, although navigation controls 50*a-f* have all been illustrated in the accompanying drawings as dedicated controls that are positioned adjacent display 52, any one or more of these controls 50*a-f* could alternatively be touchscreen controls that are displayed at one or more locations on display 52. Still further, although controls 50*a-f* have been shown herein as buttons, it will be understood that any of controls 50*a-f* could also, or alternatively, be switches, dials, or other types of non-button controls. Additionally, patient support apparatus 20 may be modified to include additional, fewer, and/or different navigation controls from the navigation controls 50*a-f* shown in FIG. 2.

Figure 3:
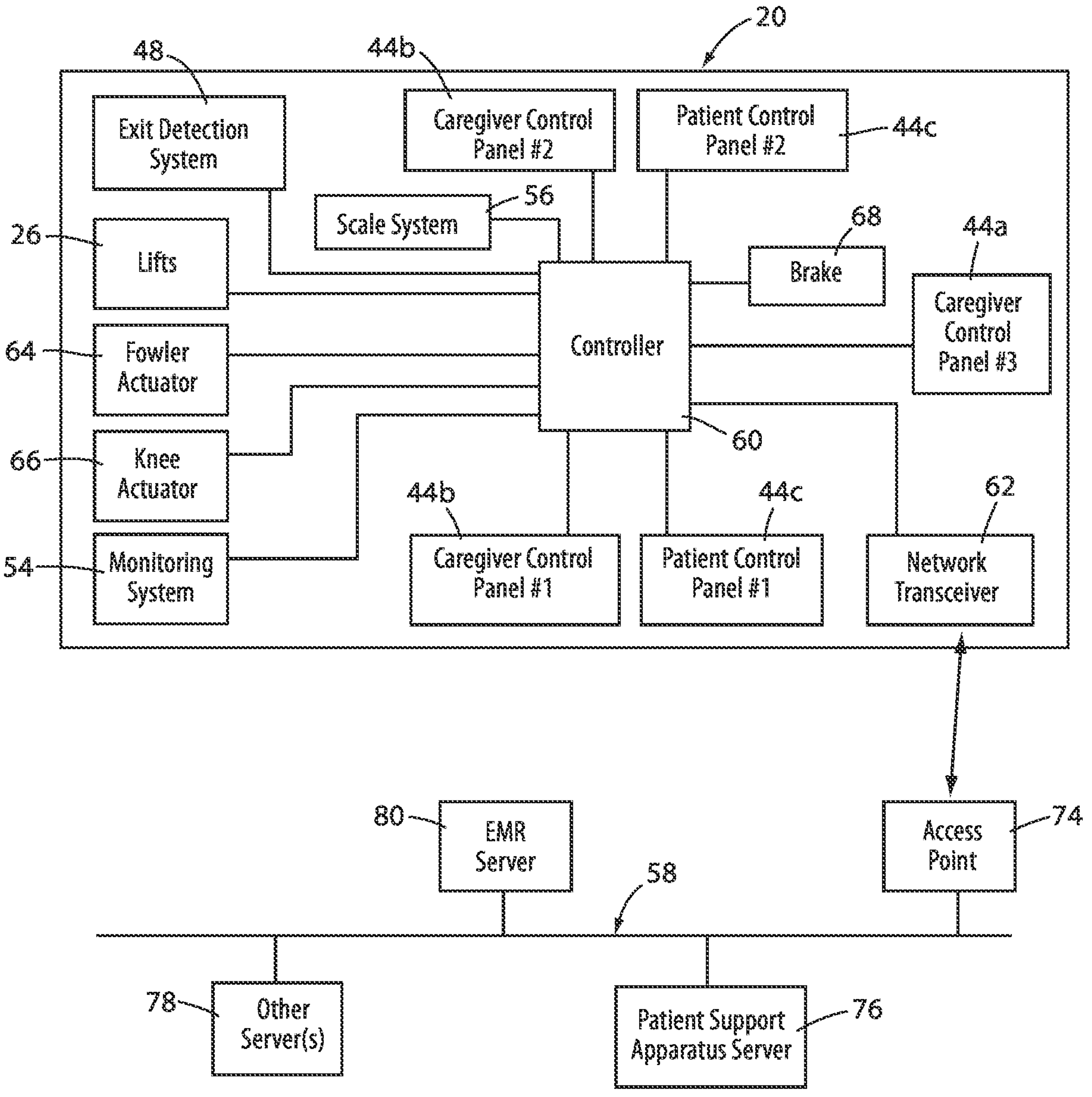
FIG. 3 is a block diagram of a control system of the patient support apparatus and an illustrative local area network that may be present in a healthcare facility.

FIG. 3 depicts a block diagram of patient support apparatus 20 and an illustrative local area network 58 that may be present in a conventional healthcare facility. Patient support apparatus 20 includes a controller 60, caregiver control panels 44*a, b*, patient control panels 44*c*, a network transceiver 62, lifts 26, exit detection system 48, scale system 56, monitoring system 54, a Fowler actuator 64, a knee or gatch actuator 66, and a brake 68.

Controller 60 may take on a variety of different forms. In the illustrated embodiment, controller 60 is implemented as a conventional microcontroller. However, controller 60 may be modified to use a variety of other types of circuits-either alone or in combination with one or more microcontrollers-such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 60 when carrying out the functions described herein, as well as the data necessary for carrying out these functions, are stored in a memory (not shown) that is accessible to controller 60.

Network transceiver 62 is, in at least some embodiments, a WiFi transceiver (e.g. IEEE 802.11) that wirelessly communicates with one or more conventional wireless access points 74 of local area network 58. In other embodiments, network transceiver 62 may be a wireless transceiver that uses conventional 5G technology to communicate with network 58, one or more servers hosted thereon, and/or other devices. In some embodiments, network transceiver 62 may include any of the structures and/or functionality of the communication modules 56 disclosed in commonly assigned U.S. Pat. No. 10,500,401 issued to Michael Hayes and entitled NETWORK COMMUNICATION FOR PATIENT SUPPORT APPARATUSES, the complete disclosure of which is incorporated herein by reference. Still other types of wireless network transceivers may be utilized.

In some embodiments, network transceiver 62 is a wired transceiver that is adapted to allow patient support apparatus 20 to communicate with network 58 via a wired connection, such as an Ethernet cable that plugs into an Ethernet port (e.g. an RJ-45 style port, an 8P8C port, etc.) built into patient support apparatus 20. In still other embodiments, patient support apparatus 20 includes both a wired transceiver 62 for communicating with network 58 via a wired connection and a wireless transceiver 62 for wirelessly communicating with network 58.

Patient support apparatus 20 is configured to use network transceiver 62 to communicate with one or more servers on the local area network 58 of a healthcare facility. One such server is a patient support apparatus server 76. Patient support apparatus server 76 is adapted, in at least one embodiment, to receive status information from patient support apparatuses 20 positioned within the healthcare facility and distribute this status information to caregivers, other servers, and/or other software applications. In some embodiments, patient support apparatus server 76 is configured to communicate at least some of the status data received from patient support apparatuses 20 to a remote server that is positioned geographically remotely from the healthcare facility. Such communication may take place via a network appliance, such as, but not limited to, a conventional router and/or a gateway, that is coupled to the Internet. The remote server, in turn, is also coupled to the Internet, and patient support apparatus server 76 may be provided with the URL and/or other information necessary to communicate with the remote server via the Internet connection between network 58 and the remove server.

Network 58 also includes an EMR server 80 (FIG. 3) that is a conventional server that stores the patients' electronic medical records. Such electronic medical records typically contain medical information about a patient, such as the patient's treatment, the patient's fall risk assessment score, a medical history, prescriptions, and/or therapies, assessments, etc. As will be discussed in further detail below, in some embodiments of patient support apparatus 20, controller 60 is adapted to request or subscribe to a patient's fall risk assessment data from EMR server 80 and use that data to automatically control one or more of the lockout functions of patient support apparatus 20.

It will be understood that the architecture and content of local area network 58 will vary from healthcare facility to healthcare facility, and that the example shown in FIG. 3 is merely one example of the type of network a healthcare facility may be employ. Typically, additional servers 92 will be hosted on network 58 and one or more of them may be adapted to communicate with patient support apparatus server 76. For example, an Admissions, Discharge, and Transfer (ADT) server, which may be a part of EMR server 80 or a separate server, is typically included on a healthcare facility's network 58. Such an ADT server is a conventional server that keeps track of patients' room assignments and, in some versions, the caregivers assigned to the patients. The ADT server is used for managing the admission, discharge, and transfer of patients in the healthcare facility. The ADT server stores patient location information, including the identity of patients and the corresponding rooms (and bay numbers in rooms with more than one patient). Patient support apparatus server 76 may be adapted to communicate with both EMR server 80 and the ADT server, and/or other servers on network 58.

Local area network 58 (FIG. 3) will also typically allow one or more electronic devices to access the local area network 58 via wireless access points 74. Such electronic devices include, but are not limited to, smart phones, tablet computers, portable laptops, desktop computers, and other types of electronic devices that include a WiFi capability and that are provided with the proper credentials (e.g. SSID, password, etc.) to access network 58.

In at least one embodiment, patient support apparatus server 76 is configured to communicate with one or more electronic devices in order to allow such devices to display the status of one or more aspects of patient support apparatus 20. In some embodiments, controller 60 is adapted to forward the status of one or more of the manual and/or automatic lockouts of patient support apparatus 20 to server 76 which, in turn, forwards this status information to one or more of these electronic devices, thereby enabling caregiver to see the status of patient support apparatus 20 on their smart phones and/or other devices.

Fowler actuator 64 (FIG. 3) is configured to change the height of a pivotable head section (e.g. Fowler section) of support deck 30. Knee actuator 66 is adapted to raise and lower the joint that couples together the thigh section and the foot section of support deck 30, thereby raising and lowering the portion of the support deck 30 that is positioned close to the patient's knees. Foot end lift 26 is configured to change the height of the foot end 40 of litter frame 28 and head end lift 26 is configured to change the height of head end 38 of litter frame 28. When both of lifts 26 are operated simultaneously and at the same speed, the height of litter frame 28 is raised or lowered without changing the general orientation of litter frame 28 with respect horizontal. When one or more of these lifts are operated at different times and/or at different speeds, the orientation of litter frame 28 is changed with respect to horizontal. Lifts 26 are therefore able to tilt litter frame 28 to a variety of different orientations, including, but not limited to, a Trendelenburg orientation and a reverse-Trendelenburg orientation. Lifts 26 and actuators 64, 66 may be electrical actuators, hydraulic actuators, or any other suitable form of powered actuators.

Brake 68 is adapted to brake and unbrake one or more of the wheels 24. When brake 68 is activated, patient support apparatus 20 is substantially prevented from moving (other than through skidding of the braked wheels 24). When brake 68 is deactivated, all wheels 24 are free to roll, thereby facilitating movement of patient support apparatus 20 to different locations. Although not shown in FIG. 3, patient support apparatus 20 includes a brake sensor for detecting the state of brake 68. As will be discussed in greater detail below, the activation and/or deactivation of brake 68 may be the triggering event of activating and/or deactivating one or more automatic motion lockouts.

Turning to FIG. 4, an illustrative caregiver control panel 44*b* comprising a plurality of controls 50 is shown. Caregiver control panel 44*b* is, in at least one embodiment, positioned on an outside face of one of the siderails 36. In the embodiment shown in FIG. 1, patient support apparatus 20 includes two caregiver control panels 44*b* (as well as two patient control panels 44*c*). Caregiver control panel 44*b* includes an angle indicator 70, a flat configuration control 50*g*, an examination position control 50*h*, a Trendelenburg control 50*i*, a reverse Trendelenburg control 50*j*, a vascular position control 50*k*, a knee up control 50*l*, a knee down control 50*m*, a Fowler up control 50*n*, a Fowler down control 500, a height up control 50*p*, a height down control 50*q*, a knee manual lockout control 50*r*, a Fowler manual lockout control 50*s*, and a manual height lockout control 50*t*. Caregiver control panel 44*b* further includes a knee lockout indicator 72*a*, a Fowler lockout indicator 72*b*, and a height lockout indicator 72*c*.

Each caregiver control panel 44*b* is in electrical communication with controller 60. When a caregiver presses on examination control 50*h*, controller 60 is configured to automatically control the movement of lifts 26 and actuators 64 and 66 to bring frame 28 and support deck 30 to a predefined examination position. Although the predefined positions of the litter frame 28 and support deck 30 may vary for a given examination position, in at least one embodiment, controller 60 is configured to move the support deck 30 and litter frame 28 to flat orientations, and to raise the height of the litter frame 28 to its maximum extent (or to a different height that makes it easy for a caregiver to exam the patient while he/she is positioned on patient support apparatus 20).

When a caregiver presses on Trendelenburg control 50*i*, controller 60 is configured to automatically control the movement of lifts 26 so as to bring litter frame 28 to a conventional Trendelenburg position. In the Trendelenburg position, the litter frame 28 is tilted so that head end 38 is positioned lower than foot end 40. The Fowler section and/or knee section of support deck 30 may be flat or raised while in the Trendelenburg position. When a caregiver presses on reverse Trendelenburg control 50*j*, controller 60 is configured to automatically control the movement of lifts 26 so as to bring litter frame 28 to a conventional reverse Trendelenburg position. In the reverse Trendelenburg position, the litter frame 28 is tilted so that foot end 40 is positioned lower than head end 38. The Fowler section and/or knee section of support deck 30 may be flat or raised while in the reverse Trendelenburg position. When a caregiver presses on vascular control 50*k*, controller 60 is configured to automatically control the movement of lifts 26 and actuators 64, 66 so as to bring litter frame 28 and deck 30 to a vascular position. In the vascular position, the Fowler section and knee section of patient support deck 30 are lowered to a flat orientation (zero degree angle with the main plane of the support deck 30) and lifts 26 are controlled so as to lower head end 38 lower than foot end 40. The vascular position is similar to the Trendelenburg position except that it also flattens the Fowler section and knee sections. Also, the angle of litter frame 28 when in the vascular position may be the same as, or different from, the angle of litter frame 28 when it is in the Trendelenburg position.

When a caregiver presses on knee up control 50*l* or knee down control 50*m*, controller 60 is configured to raise or lower, respectively, the knee section of support deck 30 by activating knee actuator 66. When a caregiver presses on Fowler up control 50*n* or Fowler down control 50*o*, controller 60 is configured to raise or lower, respectively, the Fowler section or support deck 30 by activating Fowler actuator 64. When a caregiver presses on height up control 50*p* or height down control 50*q*, controller 60 is configured to raise or lower, respectively, the height of litter frame 28 by activating lifts 26.

Lockout indicators 72*a-c* (FIG. 4) are illuminated when a corresponding control 50 has been locked out. For example, knee lockout indicator 72*a* is illuminated when the knee up or knee down controls 50*x* and 50*y* (shown in FIG. 5 and discussed more below) are locked out. Controls 50*x* and 50*y* are manually locked out when a caregiver presses on knee lockout control 50*r*. In some embodiments, knee lockout control 50*r* is a toggle switch such that repeated pressing of control 50*r* causes controller 60 to alternatingly lock and unlock controls 50*x* and 50*y*. When knee lockout control 50*r* is activated, controls 50*x* and 50*y* are locked out such that if a patient presses on knee up or knee down controls 50*x* or 50*y*, controller 60 does not activate knee actuator 66 and therefore does not raise or lower the knee section of patient support apparatus 20.

Fowler lockout indicator 72*b* (FIG. 4) is illuminated when Fowler controls 50*z* and 50*aa* on patient control panel 44*c* (FIG. 5) are locked out. Controls 50*z* and 50*aa* are manually locked out when a caregiver presses on Fowler lockout control 50*s* on caregiver control panel 44*b* (FIG. 4). As with knee lockout control 50*r*, Fowler lockout control 50*s* may be a toggle switch such that repeated pressing of control 50*s* causes controller 60 to alternatingly lock and unlock controls 50*z* and 50*aa*. When controls 50*z* and 50*aa* are locked out, if a patient presses on Fowler up or Fowler down 50*z* or 50*aa*, controller 60 does not activate Fowler actuator 64 and therefore does not raise or lower the Fowler section of support deck 30.

Height lockout indicator 72*c* (FIG. 4) is illuminated when height controls 50*bb* and 50*cc* on patient control panel 44*c* (FIG. 5) are locked out. Controls 50*bb* and 50*cc* are manually locked out when a caregiver presses on height lockout control 50*t* on caregiver control panel 44*b* (FIG. 4). As with the other manual lockout controls 50*r* and 50*s*, height lockout control 50*t* may be a toggle switch such that repeated pressing of control 50*t* causes controller 60 to alternatingly lock and unlock controls 50*bb* and 50*cc*. When controls 50*bb* and 50*cc* are locked out, if a patient presses on height up or height down control 50*bb* or 50*cc*, controller 60 does not activate lifts 26 and therefor does not raise or lower litter frame 28.

It will be understood that the locking out of a control serves to disable that control on the patient's control panel 44*c*. The locking out of a control does not disable the corresponding control on caregiver control panel 44*a* or 44*b*, in at least some embodiments. In other embodiments, controller 60 may be configured to lock out a control 50 both on the patient control panels 44*c* and the two siderail caregiver control panels 44*b*, but not lock out the corresponding control on footboard control panel 44*a*. Other arrangements of what controls are locked out on what control panels may also, or alternatively, be implemented.

Figure 5:
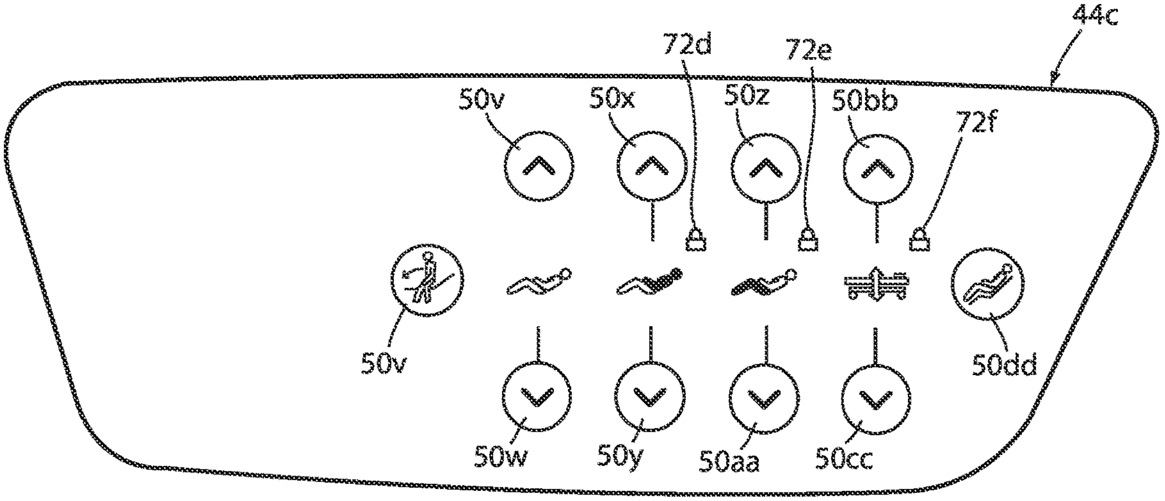
FIG. 5 is a plan view of an illustrative patient control panel of the patient support apparatus.

Turning to FIG. 5, an illustrative patient control panel 44*c* comprising a plurality of controls 50 is shown. Patient control panel 44*c* is, in at least one embodiment, positioned on an inside face of one of the siderails 36. In the embodiment shown in FIG. 1, patient support apparatus 20 includes two patient control panels 44*c*. Patient control panel 44*c* includes an exit control 50*u*, a combined Fowler and knee up control 50*v*, a combined Fowler and knee down control 50*w*, a knee up control 50*x*, a knee down control 50*y*, a Fowler up control 50*z*, a Fowler down control 50*aa*, a height up control 50*bb*, a height down control 50*cc*, and a chair control 50*dd*.

When a patient presses on exit control 50*u*, controller 60 is configured to control the operation of lifts 26, Fowler actuator 64, and knee actuator 66 to move litter frame 28 and support deck 30 to an overall configuration that makes is easier for a patient to get in or out of patient support apparatus 20. In general, this exit configuration has the Fowler section raised, the knee section flat, and the overall height of litter frame 28 at a height that is conducive for the patient to exit or enter patient support apparatus 20. When a patient presses on combined controls 50*v* or 50*w*, controller 60 is configured to raise, or lower, both the knee section and the Fowler section together. That is, if the patient presses on up control 50*v*, controller 60 is configured to activate both Fowler actuator 64 and knee actuator 66 such that both the Fowler section and the knee section are raised. If the patient presses on down control 50*w*, controller 60 is configured to activate both Fowler actuator 64 and knee actuator 66 such that both the Fowler section and the knee section are lowered.

Controls 50*x*, 50*y*, 50*z*, 50*aa*, 50*bb*, and 50*cc* of patient control panel 44*c* (FIG. 5) are the same as caregiver controls 50*l*, 50*m*, 50*n*, 500, 50*p*, and 50*q*, respectively, of caregiver control panel 44*a* (FIG. 4). That is, when a patient presses on knee up control 50*x* or knee down control 50*y*, controller 60 is configured to raise or lower, respectively, the knee section of support deck 30 by activating knee actuator 66. When a patient presses on Fowler up control 50*z* or Fowler down control 50*aa*, controller 60 is configured to raise or lower, respectively, the Fowler section or support deck 30 by activating Fowler actuator 64. When a patient presses on height up control 50*bb* or height down control 50*cc*, controller 60 is configured to raise or lower, respectively, the height of litter frame 28 by activating lifts 26.

When a patient presses on chair control 50*dd*, controller 60 is configured to control lifts 26, Fowler actuator 64, and knee actuator 66 such that the overall configuration of support deck 30 and litter frame 28 is moved to positions and orientations that resemble a chair. In general, this involves pivoting the Fowler section to a raised orientation, lowering a foot section of support deck 30 to a lowered position and, in some embodiments, tilting litter frame 28 so that head end 38 is positioned higher than foot end 40.

The lockout controls 50*r*, 50*s*, and 50*t* of the caregiver control panels 44*b* (and 44*a*), are manual lockouts that must be manually activated by a caregiver in order to be effective. As was mentioned previously, controller 60 is configured to automatically lock out one or more of the controls 50 on the patient control panels 44*c* in response to one or more triggering events. This automatic locking out occurs without the caregiver having to press any buttons on caregiver control panels 44*b* or 44*a*. In some embodiments, this automatic locking out also automatically ceases once the triggered event ceases or is otherwise absent. Thus, controller 60 is configured to automatically lock and automatically unlock certain patient controls 50 on patient control panels 44*c* in response to one or more triggering events.

The automatic locking of controls by controller 60 overrides the manually implemented state of the lockout controls, to the extent the manual and automatic lockouts differ. For example, if a lock out control 50*r*, 50*s*, and/or 50*t* is not activated, controller 60 will automatically lock out the corresponding controls 50 on patient control panel 44*c* in response to a triggering event. If a lock out control 50*r*, 50*s*, and/or 50*t* is activated when a triggering event is detected, controller 60 takes no action (except, in some embodiments, to display an automatic lockout indication) in response to a triggering event. Thus, in response to a triggering event being detected, controller 60 will automatically lock out any of the controls 50 on patient control panel 44*c* that it is programmed to automatically lock out, to the extent those controls 50 have not already been manually locked out.

The automatic unlocking of controls by controller 60, in contrast to the automatic locking of controls by controller 60, does not override the manually implemented state of the lockout controls, to the extent those states differ. In other words, when a triggering event ceases, controller 60 is configured to leave any manually activated lock outs in their locked states and to only automatically unlock those controls 50 that were previously (prior to the triggering event ceasing) in an unlocked state. Thus, for example, if none of lock out control 50*r*, 50*s*, and/or 50*t* were manually activated at the time a triggering event ceased, controller 60 is configured to automatically unlock the controls on patient control panel 44*c* that correspond to the functions of controls 50*r*, 50*s*, and/or 50*t*. However, if, for example, all of controls 50*r*, 50*s*, and 50*t* were manually activated prior to the triggering event ceasing, controller 60 is configured, in response to the triggering event ceasing, configured to leave the controls 50 on patient control panel 44*c* corresponding to lockout controls 50*r-t* in their locked out state.

The particular control(s) 50 on patient control panel 44*c* that are automatically locked out by controller 60 may vary and, in some embodiments, are customizable by a caregiver, as will be discussed in further detail below. In addition, the triggering event(s) that cause controller 60 to automatically lock and unlock the corresponding controls 50 on patient control panels 44*c* may also vary and, in some embodiments, be customizable by the caregiver. In general, such triggering events includes, but are not limited to, any one or more of the following: the activation of the exit detection system 48, the selection of a particular sensitivity of exit detection system 48, the activation of monitoring system 54, the taking of a patient weight reading using scale system 56, the zeroing of scale system 56, the activation of brake 68, the receipt of a patient's fall risk score that is above a threshold, the entry of one or more of the caregiver control panels 44*a* and/or 44*b* into a sleep state, the expiration of a timer, the absence of the patient from the patient support apparatus 20, the movement of the support deck 30 and/or litter frame 28 to a particular configuration, the height of the litter frame 28 exceeding a threshold, and/or other events.

In some embodiments, controller 60 is configured to automatically lock out the height controls 50*bb* and 50*cc* on the patient control panels 44*c* in response to the occurrence of a triggering event. In other embodiments, controller 60 is configured to automatically lock out only the height raising control 50*bb* in response to the triggering event and to leave the height lowering control 50*cc* operable. In these latter embodiments, controller 60 reacts to the triggering event by preventing the patient from raising the height of litter frame 28 (via control 50*bb*), but allows the patient to lower the height of litter frame 28 (via control 50*cc*). In still other embodiments, controller 60 may be configured to automatically lock out height raising control 50*bb* in response to a triggering event only if the current height of the litter frame 28 exceeds a particular threshold. In such embodiments, controller 60 only locks out the height control 50*bb* if, or when, the height of the litter frame 28 exceeds the threshold height. This allows the patient to use height raising control 50*bb* until the threshold height is reached, but stops movement of the litter frame 28 at that threshold height and prevents the patient from raising the height any further.

As will be discussed in greater detail below, controller 60 may also, or alternatively, be configured to lock out any one or more of the other controls 50*v*-50*aa* and/or 50*dd* on patient control panel 44*c* in response to triggering event, either in combination with, or separately from, the locking of height control(s) 50*bb* and/or 50*cc*. For example, in some embodiments, controller 60 is configured to automatically lock out a brake control (not shown) that may be present on caregiver control panels 44*b* and/or 44*c* in response to a triggering event. If the brake control is a toggle control, controller 60 may be configured to automatically lock out the brake control after the brake is triggered, thereby preventing the brake from being turned off when the triggering event is detected. If there is a separate control for activating and deactivating the brake, then controller 60 may be configured to automatically lock out the deactivating control. In such embodiments, for example, controller 60 may be configured to automatically lock out the brake control (whether it is a toggle control or includes separate controls for activation/deactivation) such that the brake cannot be deactivated whenever controller 60 detects that the exit detection system 48 is armed, and/or whenever the monitoring system is 54 is armed, and/or whenever the patient is positioned at a location on the perimeter of the litter frame, and/or in response to yet another triggering event. Still other controls, whether on patient control panels 44*c* and/or caregiver control panels 44*a* and/or 44*b* may also, or alternatively, be automatically locked out by controller 60 in response to one or more triggering events.

Figure 2:
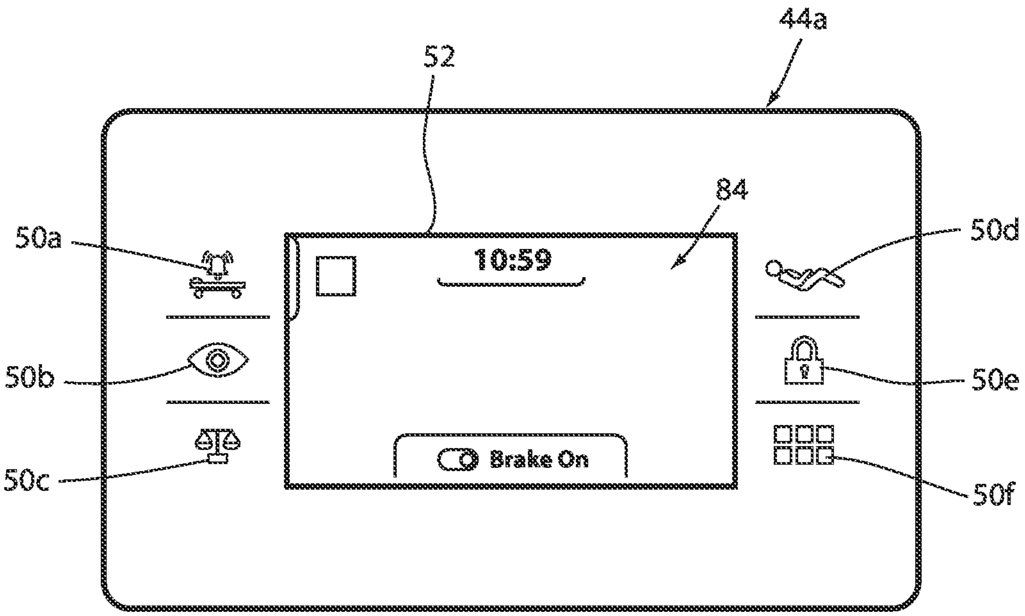
FIG. 2 is a plan view of a first illustrative caregiver control panel of the patient support apparatus.
Figure 6:
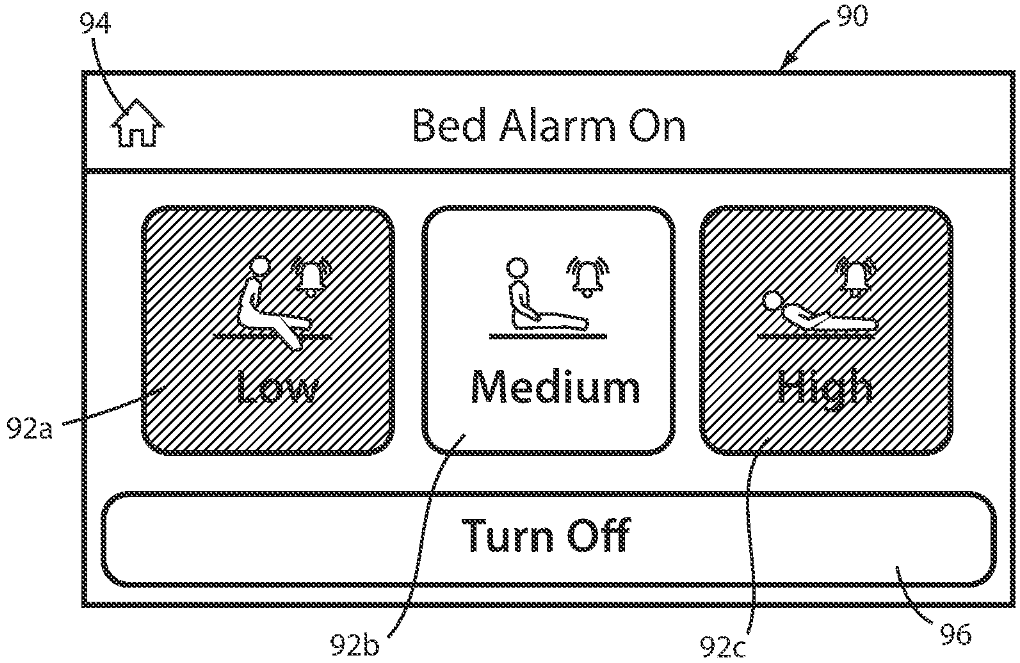
FIG. 6 is an illustrative exit detection system control screen that may be displayed on a display of the patient support apparatus.

FIG. 6 illustrates a first example of a triggering event that controller 60 may be configured to automatically detect. FIG. 6 illustrates an example of an exit detection system control screen 90. In some embodiments, controller 60 is configured to display exit detection system control screen 90 on display 52 in response to a user pressing on exit detection control 50*a* (FIG. 2). Alternatively, or additionally, controller 60 may be configured to allow a user to navigate to exit detection system control screen 90 in other manners. However reached, exit detection system control screen 90 allows a user to arm or disarm exit detection system 48, as well as to select a sensitivity level for exit detection system 48. As shown in FIG. 6, exit detection system control screen 90 includes a low sensitivity selector 92*a*, a medium sensitivity selector 92*b*, and a high sensitivity selector 92*c*. Exit detection system control screen 90 further includes a home control 94 and a turn off control 96.

When the caregiver presses home control 9 (FIG. 6), controller 60 is configured to display a home screen on display 52. One example of a home screen 84 is illustrated in FIG. 2. Other types of home screens may be implemented. When the caregiver presses the turn off control 96, controller 60 is configured to disarm exit detection system 48. When the caregiver presses the low sensitivity selector 92*a*, controller 60 is configured to arm exit detection system 48 with a low sensitivity level. When the caregiver presses the medium sensitivity selector 92*b*, controller 60 is configured to arm exit detection system 48 with a medium sensitivity level. When the caregiver presses the high sensitivity selector 92*c*, controller 60 is configured to arm exit detection system 48 with a high sensitivity level. The sensitivity level refers to the amount of movement that is required to for the patient to trigger an exit detection alarm. Thus, for example, if the low sensitivity level 92*a* is selected, exit detection system 48 is configured to issue an exit alert only when the patient has shifted his or her body such that they are partially out of patient support apparatus 20. If the medium sensitivity level 92*b* is selected, exit detection system 48 is configured to issue an exit alert before the patient shifts his or her body partially out of patient support apparatus 20. If the high sensitivity level 92*c* is selected, exit detection system 48 is configured to issue an exit alert in response to the patient moving only a small amount (i.e. less than the amount of movement necessary to trigger an exit alert for either the medium or low sensitivity levels 92*a* or 92*b*).

In some embodiments, the sensitivity levels 92*a*-92*c* are implemented by changing the boundaries of a zone in which the patient's center of gravity must remain in order to prevent an exit alert from occurring. In such embodiments, low sensitivity level 92*a* corresponds to a zone having the greatest area, high sensitivity level 92*c* corresponds to a zone having the smallest area, and medium sensitivity level corresponds to a zone having an area in between the two. Further details regarding several manners in which exit detection system 48 may be configured to implement such sensitivity levels, as well as other aspects that may be incorporated into exit detection system 48, are found in commonly assigned U.S. patent application Ser. No. 63/255,211 filed Oct. 13, 2021, by inventors Sujay Sukumaran et al. and entitled PATIENT SUPPORT APPARATUS WITH AUTOMATIC SCALE FUNCTIONALITY, and commonly assigned U.S. patent application Ser. No. 16/917,004 filed Jun. 30, 2020, by inventors Sujay Sukumaran et al. and entitled PERSON SUPPORT APPARATUS WITH ADJUSTABLE EXIT DETECTION ZONES, the complete disclosure of both of which are incorporated herein by reference.

As was mentioned, in at least one embodiment, controller 60 is configured to automatically lock out at least one control on patient control panels 44*c* in response to a caregiver activating exit detection system 48. In this embodiment, controller 60 automatically locks out the one or more controls regardless of which sensitivity level 92*a*-*c* the caregiver selects. In another embodiment, controller 60 automatically locks out the one or more controls 50 on the patient control panels 44*c* if the caregiver arms the exit detection system 48 with the medium or high sensitivity levels 92*b* or 92*c*. In still other embodiments, the automatic locking out of one or more controls 50 on the patient control panels 44*c* may occur in response to different selections of the sensitivity levels 92*a*-92*c*. Regardless of which sensitivity level(s) trigger the automatic lock outs, controller 60 is configured to terminate the automatic lock outs in response to the caregiver disarming the exit detection system 48 (i.e. in response to the user pressing on turn off control 96).

Figure 7:
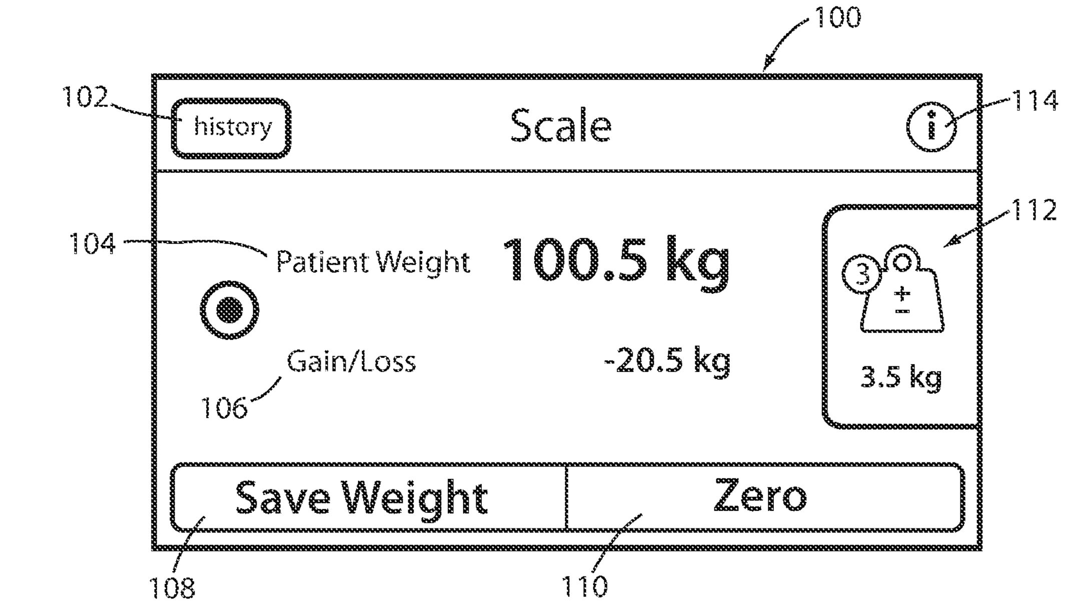
FIG. 7 is an illustrative scale system control screen that may be displayed on the display of the patient support apparatus.

FIG. 7 illustrates a second example of one or more triggering events that controller 60 may be configured to automatically detect. FIG. 7 illustrates an example of a scale control screen 100. In some embodiments, controller 60 is configured to display scale control screen 100 on display 52 in response to a user pressing on scale control 50*c* (FIG. 2). Alternatively, or additionally, controller 60 may be configured to allow a user to navigate to scale control screen 100 in other manners. However reached, scale control screen 100 allows a user to take a patient weight reading and/or control other aspects of scale system 56. As shown in FIG. 7, scale control screen 100 includes a scale history control 102, a patient weight indicator 104, a gain/loss indicator 106, a save weight control 108, a scale zero control 110, an equipment log indicator 112, and an information control 114.

When a caregiver presses scale history control 102, controller 60 is configured to display a history of previous patient weight readings. In some embodiments, the patient weight readings may be graphed with the times of the previous weight readings shown on an X-axis and the value of the patient weight readings shown on a Y-axis. Alternatively, or additionally, the previous patient weight readings may be displayed in a list format.

Patient weight indicator 104 indicates the patient's currently sensed weight. Gain/loss indicator 106 indicates the amount of weight that the patient gained or lost since the previously saved patient weight reading. Save weight control 108, when pressed, causes controller 60 to record the current weight reading (shown by weight indicator 104) in a memory onboard patient support apparatus 20, and to add the weight reading to the weight history that is accessible in response to pressing on scale history control 102. In some embodiments, controller 60 is configured to automatically lock out one or more of the controls on patient control panels 44*c* in response to the caregiver pressing on save weight control 108. In other words, in some embodiments, the pressing of control 108 is an auto-lock triggering event.

In such embodiments, controller 60 continues to keep such controls on patient control panels 44*c* locked out until the weight saving function of control 108 is completed. In some embodiments, it may take several seconds for a stable patient weight reading to be detected and recorded in response to activating save weight control 108. During that time period, controller 60 may automatically lock out one or more of the controls on patient control panels 44*c* that cause movement of one or more components of patient support apparatus 20. By locking out these controls during the weight recording process, movement by the patient of the support deck 30 and/or litter frame 28 is prohibited, thereby helping to ensure that a stable weight reading can be detected by scale system 56 during this process. In other words, the automatic lockout that controller 60 activates in response to the caregiver pressing the save weight control 108 reduces the ability of the patient to disrupt the weight recording process.

Scale zero control 110 (FIG. 7), when pressed, causes controller 60 to zero the scale system 56. That is, controller 60 is configured to record the tare weight on patient support apparatus 20 when the zero control 110 is pressed, and to thereafter subtract that tare weight from whatever the current scale reading is in order to accurately display only the weight of the patient. In some embodiments of patient support apparatus 20, controller 60 is configured to automatically lock out one or more of the controls on patient control panels 44*c* in response to the scale zero control 110 being pressed. Thus, the pressing of scale zero control 110 is an auto locking triggering event, in at least some embodiments. The automatic locking of one or more controls 50 on patient control panels 44*c* in response to zero control 110 being pressed lasts for as long as it takes to the zero the scale system 56. In general, this zeroing process typically may take on the order of five to fifteen seconds, although other time periods may be required. Regardless of the length of the zeroing process, by automatically locking out one or more of the controls 50 on patient support apparatus 20, controller 60 reduces the chances that movement of the support deck 30 and/or litter frame 28 will lead to disruptive scale readings. Once the zeroing process is over, controller 60 is configured to return the controls 50 on patient control panels 44*c* to the state to which they had previously been manually set.

In some embodiments, controller 60 is configured to not only automatically lock out the motion controls on patient control panels 44*c* in response to the pressing of save weight control 108 and/or zeroing control 110 (FIG. 7), but it is also configured to automatically lock out the motion controls on caregiver control panels 44*a* and 44*b* as well. In such embodiments, the locking out of motion controls on all of the control panels 44*a-c* during the weight reading process and/or during the scale zeroing process reduces the chances that movement of the litter frame 28 and/or support deck 30 will disrupt either or both of these processes. When such caregiver controls are also locked out during these processes, controller 60 is configured to automatically return these caregiver controls to the unlocked state in response to the completion of the weight reading process and/or the scale zeroing process.

Equipment log control 112 (FIG. 7), when pressed, activates an equipment logging function that keeps track of the weight and number of pieces of equipment that have been added to the patient support apparatus 20 since the scale system was zeroed. The weight of the pieces of equipment maintained in this log is subtracted from the overall weight recorded by scale system 56 to determine the patient's actual weight (the tare weight is also subtracted from this overall weight reading). In some embodiments, equipment log control 112 may operate in any of the same manners as, and/or include any of the same functions as, the equipment logging system disclosed in commonly assigned U.S. patent application Ser. No. 16/992,515 filed Aug. 13, 2020, by inventors Kurosh Nahavandi et al. and entitled PATIENT SUPPORT APPARATUS WITH EQUIPMENT WEIGHT LOG, the complete disclosure of which is incorporated herein by reference.

In some embodiments of patient support apparatus 20, the addition or removal of a piece of equipment from the equipment weight log is carried out manually by the caregiver pressing on a control for adding or removing equipment from the weight log. In such embodiments, controller 60 may be configured to automatically lock out one or more controls 50 on patient control panels 44*c* when the control for changing the equipment weight log is activated. In this manner, movement of the patient support apparatus 20 due to a patient activating a motion control on one of patient control panels 44*c* is prevented during the process of changing the equipment weight log. This helps prevent weight disturbances from interfering with the changes made to the equipment weight log. Once the weight log has been updated, controller 60 may be configured to automatically return the patient controls to their previous state.

Information control 114 (FIG. 7), when pressed, causes controller 60 to display additional information about scale system 56, such as its classification, individual load cell readings, the date the system was last zeroed, and/or other information.

Figure 8:
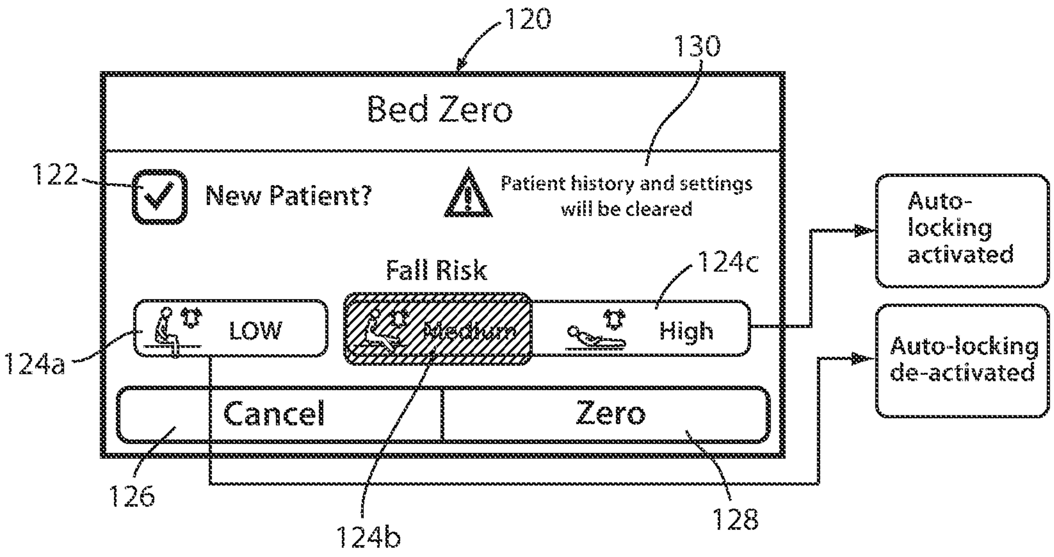
FIG. 8 is an illustrative new patient control screen that may be displayed on the display of the patient support apparatus.

FIG. 8 illustrates a third example of one or more triggering events that controller 60 may be configured to automatically detect. FIG. 8 illustrates an example of a new patient screen 120. In some embodiments, controller 60 is configured to display new patient screen 120 on display 52 in response to a user pressing on scale zero control 110 (FIG. 7). Alternatively, or additionally, controller 60 may be configured to allow a user to navigate to new patient screen 120 in other manners. However reached, new patient control screen 120 allows a user to input a patient's fall risk score into patient support apparatus 20.

As shown in FIG. 8, new patient screen 120 includes a new patient control 122, a low fall risk selector 124*a*, a medium fall risk selector 124*b*, a high fall risk selector 124*c*, a cancel control 126, a scale zero control 128, and an information window 130. New patient control 122 is selected by a caregiver when a new patient is assigned to patient support apparatus 20. Controller 60, in response to the caregiver selecting new patient control 122, is configured to clear from its memory all of the settings and/or data associated with the previous patient, including, for example, prior weight readings that were saved for the previous patient. Low fall risk selector 124*a* is selected by the caregiver when the patient is considered to have a low risk of falling. Medium fall risk selector 124*b* is selected by the caregiver when the patient is considered to have a medium risk of falling. And high fall risk selector 124*c* is selected by the caregiver when the patient is considered to have a high risk of falling.

The fall risk of a particular patient may be determined in different manners. In some situations, the fall risk is determined using a conventional fall risk assessment, such as the Morse fall risk scale or the Conley fall risk scale. In such situations, the particular healthcare facility in which patient support apparatus 20 is positioned may have guidelines for converting the assessment score into a low, medium, or high fall risk category. Patient support apparatus 20 may be configured to allow the caregiver to manually enter the fall risk by pressing on one of the selectors 124*a-c*, and/or it may be configured to automatically retrieve the patient's fall risk score from EMR server 80. When configured to retrieve the patient's fall risk score from EMR server 80, patient support apparatus 20 utilizes network transceiver 62 and, in some embodiments, patient support apparatus server 76. In such embodiments, patient support apparatus 20 may be configured to communicate with a short range locator unit that sends it location information. Patient support apparatus 20 forwards this location information to patient support apparatus server 76 which uses the location information to determine the room and/or bay in which patient support apparatus 20 is located. From its communications with EMR server 80 and/or a separate ADT server, patient support apparatus server 76 is able to use the room and/or bay of patient support apparatus 20 to determine the particular patient assigned to patient support apparatus 20. Once the particular patient assigned to patient support apparatus 20 is determined, that patient's fall risk record in EMR server 80 is retrieved and forwarded to patient support apparatus 20 via network transceiver 62. Further details of the manner in which patient support apparatus 20 and/or patient support apparatus server 76 determine the patient assigned to that patient support apparatus 20 are found in commonly assigned U.S. patent application Ser. No. 17/622,593 filed Dec. 23, 2021, by inventors Thomas Durlach et al. and entitled CAREGIVER ASSISTANCE SYSTEM, and commonly assigned U.S. Pat. No. 1,162,585 issued Jul. 13, 2021, to inventors Thomas Durlach et al. and entitled PATIENT CARE SYSTEM, the complete disclosures of both of which are incorporated herein by reference.

Regardless of whether patient support apparatus 20 is informed of the patient's fall risk score through the caregiver manually entering it via screen 120 (FIG. 8) or patient support apparatus 20 automatically retrieving it from EMR server 80, controller 60 is configured, in some embodiments, to consider the fall risk score a triggering event for the auto locking function if the fall risk score exceeds a threshold. In other words, if the patient has a fall risk above a threshold, controller 60 is configured in some embodiments to automatically lock out one or more of the controls 50 on the patient control panels 44*c*. In the embodiment illustrated in FIG. 8, controller 60 is configured to automatically lock out one or more of the controls 50 on control panels 44*c* when the patient's fall risk is considered either medium or high. If the patient's fall risk score is considered low, controller 60 does not automatically lock out any of the controls on patient control panels 44*c* (unless one or more other triggering events take place). It will be understood that the particular fall risk threshold that triggers the automatic lock out function may be varied. Thus, for example, in some embodiments, controller 60 may be configured to automatically lock out certain controls on patient control panels 44*c* only when the patient's fall risk is considered high and to leave those controls unlocked if the patient's fall risk is medium or low. Still other thresholds may be used.

When controller 60 automatically locks out one or more controls 50 on patient control panels 44*c* in response to the patient's fall risk score, controller 60 maintains those controls in the locked out state until the patient's fall risk is re-assessed and reduced to a level below the fall risk threshold (or until a new patient is assigned to the patient support apparatus 20). If the patient's fall risk does not change to a level below the threshold, controller 60 may keep the locked out controls in a locked out state for the patient's entire visit to the healthcare facility.

Cancel control 126 of new patient control screen 120 (FIG. 8) instructs controller 60 to cancel the new patient function when the caregiver presses on control 126. In other words, controller 60 does not erase the settings and patient data currently stored in memory when the caregiver presses on cancel control 126. If the caregiver presses on zero control 128, controller 60 is configured to automatically zero scale system 56 in the manner previously described. Information window 130 displays information to the caregiver regarding the new patient function. In the example shown in FIG. 8, this information informs the caregiver that activating the patient function will erase the previous patient's history and settings.

Controller 60 may also, or alternatively, be configured automatically lock out one or more of the controls 50 on patient control panels 44*c* in response to other triggering events besides those associated with the screens of FIGS. 6-8. That is, in some embodiments, controller 60 may be configured to automatically lock out one or more patient controls in response to the activation of monitoring system 54, the activation of brake 68, the entry of one or more of the caregiver control panels 44*a* and/or 44*b* into a sleep state, the expiration of a timer, the absence of the patient from the patient support apparatus 20, the movement of the support deck 30 and/or litter frame 28 to a particular configuration, the height of the litter frame 28 exceeding a threshold, the absence of the caregiver from the room or bay in which the patient support apparatus 20 is positioned, the patient moving to a particular position on the patient support apparatus 20, display 52 being manually or automatically locked, equipment being added to—or removed from—the patient support apparatus, a propulsion system onboard patient support apparatus 20 being activated, and/or still other triggering events. These triggering events will now be described in more detail.

In some embodiments, when a person activates monitoring system 54, controller 60 is configured to automatically lock out one or more of the controls 50 on patient control panels 44*c*. As was noted, monitoring system 54 is adapted to monitor a plurality of conditions of patient support apparatus 20 and issue an alert is any one or more of the plurality of conditions are in an undesired state. For example, in some embodiments, monitoring system 54 monitors the current state of each of the siderails 36, brake 68, the height of litter frame 28, and the state of exit detection system 48. If more than a desired number of siderails 36 are in their lowered positions, or if the brake is not activated, or if the height of the litter frame is above a threshold, or if exit detection system 48 is not armed, monitoring system 54 is adapted to issue an alert. In some embodiments, monitoring system 54 may automatically be armed unless a caregiver disarms it. However, regardless of whether armed automatically by a caregiver or by controller 60, controller 60 is configured in some embodiments to automatically lock out one or more patient controls 50 on control panels 44*c* in response to the arming of monitoring system 54.

In some embodiments, controller 60 is configured to automatically lock out one or more controls 50 on patient control panels 44*c* in response to the brake 68 being in a particular state. For example, in some such embodiments, controller 60 automatically locks out the one or more patient controls when brake 68 is not activated. In other embodiments, controller 60 may automatically lock out the one or more patient controls in response to brake 68 being activated.

In some embodiments, controller 60 is configured to automatically lock out one or more controls 50 on patient control panels 44*c* in response to one or more of the controls panels 44 entering a sleep state. That is, in some embodiments, one or more of the control panels 44 are configured to enter a sleep state when they are not used for a predetermined amount of time (which may vary from embodiment to embodiment, but may generally be in the range of half a minute or so to around two minutes). For example, in some embodiments, controller 60 is configured to automatically place display 52 and caregiver control panel 44*a* in a sleep state after a predetermined time period of disuse. When this sleep state is entered, the caregiver has to perform a wake up action before he or she is able to utilize control panel 44*a*. The particular wake up action may vary from embodiment to embodiment. In some embodiments, the wake up action is the entering of a passcode or taking some other action that is generally not known to the patient and/or visitors of the patient. In other embodiments, the wake up action may simply require the caregiver to slide an icon across the screen, perform a swiping action on the touchscreen display 52, and/or take another action. In some embodiments, the wake up action may take on the form of any of the actions for unlocking the lock screen disclosed in commonly assigned U.S. patent application Ser. No. 63/255,240 filed Oct. 13, 2021, by inventors Sujay Sukumaran et al. and entitled PATIENT SUPPORT APPARATUS WITH LOCKING FEATURES, the complete disclosure of which is incorporated herein by reference. Regardless of the specific wake up action that is required to end the sleep state of the one or more control panels 44, controller 60 is configured to automatically return the patient controls to their previous state when the control panel is woken up. This previous state may refer to a manually locked state (if the caregiver had previously manually locked the one or more controls), or it may refer to an unlocked state (if the caregiver had not previously manually locked the one or more controls).

In at least one embodiment, controller 60 is configured to automatically lock out not only one or more patient controls 50 on patient control panels 44*c* in response to caregiver control panel 44*a* going to sleep, but also one or more caregiver controls 50 on caregiver control panels 44*b*. In this embodiment, when control panel 44*a* goes to sleep, both caregiver control panels 44*b* and patient control panels 44*c* have one or more of their controls locked out. This prevents any person from using these particular controls unless they possess the knowledge required to wake up caregiver control panel 44*a*. This type of automatic lock outs may be useful in situations where the caregiver doesn't want the patient to be able to reach over a siderail 36 and use the caregiver controls of caregiver control panels 44*b* when the caregiver is absent from the room.

In some embodiments, controller 60 is configured to automatically lock out one or more patient controls 50 on patient control panels 44*c* in response to one of the caregiver control panels 44*a* and/or 44*b* being put into a locked state. The locked state may be manually activated by a caregiver or, in some embodiments, automatically implemented by controller 60. The locked state is similar to the sleep state mentioned above except that it cannot be unlocked without taking an action that is known only to a caregiver. In other words, unlike the sleep state, which may be awoken from in some embodiments through a simple swiping or press-and-hold action, the unlocking of a caregiver control panel from the locked state requires a password, a passcode, a caregiver ID, or some other information to be input into the patient support apparatus 20 that is not likely to be known by the patient, but instead is known by the caregiver. In some embodiments, when any one of the caregiver controls panels 44*a* and/or 44*b* are put into a locked state, controller 60 is configured to automatically put the other caregiver control panels 44*a* and/or 44*b* into the locked state. Further, when the caregiver unlocks one of the control panels 44*a* and/or 44*b*, controller 60 may be configured to automatically unlock the other caregiver control panels 44*a* and/or 44*b*. In this manner, all of the caregiver control panels 44*a* and 44*b* are locked and unlocked in unison with each other.

In some embodiments, controller 60 is configured to automatically lock out one or more patient controls 50 on patient control panels 44*c* in response to the movement of support deck 30 and/or litter frame 28 to one or more predetermined positions. For example, in some embodiments, controller 60 is configured to automatically lock out one or more of the controls 50 on patient control panels 44*c* in response to the caregiver moving patient support apparatus 20 to a Trendelenburg position (using, for example, control 50*i*), or in response to the caregiver moving patient support apparatus 20 to a reverse-Trendelenburg position (using, for example, control 50*j*), or to still another configuration (e.g. the vascular position of control 50*k*, the examination position of control 50*h*, the flat position of control 50*g*, a low height configuration, and/or another configuration). Alternatively, or additionally, controller 60 may be configured to automatically lock out one or more controls 50 on patient control panels 44*c* when support deck 30 and/or litter frame 28 are moved to a jackknife position, a kidney position, a prone position, a lithotomy position, a Sim's position, a lateral position, a supine position, a Fowler's position, and/or a high Fowler's position.

In some embodiments, controller 60 is configured to automatically lock out one or more patient controls 50 on patient control panels 44*c* in response to the raising of litter frame 28 above a threshold height. In some such embodiments, controller 60 is configured to automatically lock out the height raising control 50*bb* (FIG. 5) when the height of litter frame 28 reaches the threshold height, thereby effectively limiting the patient's ability to raise litter frame 28 above the threshold height. Controller 60 may be configured to additionally, or alternatively, lock out other patient controls 50 on patient control panels 44*c* in response to litter frame 28 exceeding the threshold height. In such embodiments, one or more sensors are included on patient support apparatus 20 that measure how far lifts 26 have extended, or that measure one or more other parameters that can be used to determine the current height of litter frame 28.

In some embodiments, controller 60 is configured to automatically lock out one or more patient controls 50 on patient control panels 44*c* in response to the patient being absent from patient support apparatus 20. In such embodiments, scale system 56 may be configured to take automatic and repeated measurements of the weight onboard patient support apparatus 20 and use those readings to determine if a patient is present on patient support apparatus 20 or not. When not patient is onboard, scale system 56 informs controller 60 of this fact and controller 60 automatically locks out one or more of the controls 50 on patient control panels 44*c*.

In some embodiments, controller 60 is configured to automatically lock out one or more patient controls 50 on patient control panels 44*c* in response to the caregiver being absent from the vicinity of patient support apparatus 20. In such embodiments, patient support apparatus 20 is configured to automatically detect the presence of a caregiver within the vicinity of patient support apparatus 20. In some such embodiments, each caregiver wears an RF ID tag, or other items, whose location can be detected by one or more sensors positioned onboard patient support apparatus 20. Alternatively, or additionally, the location of the RF ID tag worn by the caregiver may be detected by an independent real time location system (RTLS) that includes a server hosted on local area network 58. In such embodiments, the RTLS server shares the location of the caregivers with patient support apparatus server 76, which in turn reports these locations to the patient support apparatuses 20 using network transceiver 62. In these embodiments, the patient support apparatus 20 does not need to include any sensors for detecting the presence/absence of the caregiver, but instead is informed of the caregiver's presence through messages received from patient support apparatus server 76.

In some embodiments, patient support apparatus 20 may include a plurality of ultra-wideband transceiver that are adapted to use ultra-wideband (UWB) RF communications with a UWB tag worn by, or coupled to, the caregivers. In such systems, patient support apparatus 20 uses the UWB communications to determine if the caregiver's tag is positioned within a predefined volume of space surrounding the patient support apparatus 20. If the caregiver is not positioned within that vicinity, controller 60 is configured to automatically lock out one or more of the controls on patient control panel 44*c*. Further details regarding the manner in which patient support apparatus 20 may be constructed to determine the location of UWB tags worn by caregivers, and thus their absence or presence within the vicinity of patient support apparatus 20, are disclosed in commonly assigned U.S. patent application Ser. No. 63/306,279 filed Feb. 3, 2022, by inventors Madhu Thota et al. and entitled COMMUNICATION SYSTEM FOR PATIENT SUPPORT APPARATUSES, the complete disclosure of which is incorporated herein by reference.

In some embodiments, patient support apparatus 20 may be further configured to detect the relative position of one or more medical devices using UWB communications and, if the medical device is positioned within a predefined proximity to patient support apparatus 20, to automatically lock out one or more of the controls on patient control panels 44*c*. For example, in some embodiments, controller 60 may be configured to automatically lock out all of the movement controls on patient control panels 44*c* when a ventilator is being used with the patient. The detection of the use of the ventilator with the patient may be based on UWB communications in any of the manners disclosed in the aforementioned '279 patent application. Alternatively, controller 60 may be configured to lock out the patient controls on patient control panel 44*c* (e.g. control 50*aa*) that would otherwise allow the patient to lower the Fowler angle to an angular orientation of less than thirty-degrees (or some other angle). Still other types of automatic lock outs may be implemented by controller 60 in response to detecting other types of medical devices that are associated with patient support apparatus 20 and/or with the patient, as detected through UWB communications or through another location technology.

In some embodiments, controller 60 is configured to automatically lock out one or more patient controls 50 on patient control panels 44*c* in response to an onboard propulsion system (not shown) being activated. Such an onboard propulsion system is adapted to provide power to one or more of the wheels 24 (or to another wheel not shown in FIG. 1) so that the caregiver does not need to exert as much effort when pushing the patient support apparatus 20 from one location to another. Examples of some suitable propulsion systems are disclosed in commonly assigned U.S. Pat. No. 10,507,145 issued Dec. 17, 2019, to DeLuca et al. and entitled POWERED PATIENT SUPPORT APPARATUS, and U.S. Pat. No. 10,603,234 issued Mar. 31, 2020, to Thomas Puvogel et al. and entitled PATIENT SUPPORT APPARATUSES WITH DRIVE SYSTEMS, the complete disclosures of both of which are incorporated herein by reference. Other types of propulsion systems may also, or alternatively, be incorporated into patient support apparatus 20.

In those embodiments with an onboard propulsion system, controller 60 may be configured to automatically lock out one or more of the controls 50 on patient control panels 44*c* in response to the activation of the propulsion system and/or in response to movement of the patient support apparatus 20 by the propulsion system. In other words, the triggering event may be the mere act of turning on or otherwise activating the propulsion system, or it may be the act of actually driving the patient support apparatus 20. In either situation, controller 60 is configured to return the one or more patient controls to their previous state in response to the propulsion system being turned off or in response to driving movement of the patient support apparatus 20 terminating.

In some embodiments, controller 60 is configured to automatically lock out one or more patient controls 50 on patient control panels 44*c* in response to a successful pairing between patient support apparatus 20 and one or more devices, and/or in response to an absence of pairing between patient support apparatus 20 and one or more devices. For example, in some embodiments, patient support apparatus 20 may be configured to include a Bluetooth transceiver, or other type of transceiver, that can be paired with another device when the device is positioned within proximity to patient support apparatus 20. In such embodiments, controller 60 may be configured to automatically lock out one or more controls on patient control panels 44*c* in response to the other device successfully pairing with patient support apparatus 20, or in response to the other device not being paired with the patient support apparatus 20. In some such embodiments, caregivers may wear a wristband, or other Bluetooth-enabled device, that automatically pairs with the patient support apparatus 20 when they are positioned nearby to patient support apparatus 20. In such embodiments, controller 60 may automatically lock out one or more of the controls on patient control panels 44*c* when the pairing with a caregiver-worn Bluetooth device is absent. Still other types of devices may pair with patient support apparatus 20 and the presence, or absence, of that pairing may be interpreted by controller 60 as a triggering event for locking one or more of the controls on patient control panels 44*c*.

In some embodiments, controller 60 is configured to automatically lock out one or more patient controls 50 on patient control panels 44*c* in response to movement of the patient to one or more predefined positions on patient support apparatus 20. For example, in some embodiments, controller 60 is configured to automatically lock one or more of the controls on patient control panels 44*c* in response to the patient moving to an outer perimeter of the patient support apparatus 20 (e.g. at or near the outer perimeter of the support deck 30). In such embodiments, scale system 56 and/or exit detection system 48 may be adapted to repetitively and automatically compute the location of the patient based upon outputs from a plurality of force sensors, such as load cells, that are built into the patient support apparatus 20. The location may comprise the center of gravity of the patient, or it may comprise other parameters. Regardless of how it is quantified, controller 60 may be configured to automatically lock out the one or more controls in response to the patient moving to the outer perimeter of support deck 30.

Such automatic locking out of these one or more controls may be beneficial in helping to prevent patient falls since movement of the patient support apparatus 20 is prohibited (through the locked out controls) while the patient is near the edge of patient support apparatus 20. This automatic locking out of one or more patient controls in response to changes in the position of the patient may be carried out independently of the alarms issued by exit detection system 48. That is, whether exit detection system is armed or not, controller 60 may be configured to automatically lock out one or more controls based on the patient's position, and the patient's positions that trigger this automatic locking out may be different from the positions that trigger an exit detection alert.

Although the automatic locking out of certain controls has so far been described as primarily applying to patient control panels 44*c*, it will be understood that controller 60 may be modified in some embodiments of patient support apparatus 20 to automatically lock out patient controls that are not built into patient support apparatus 20. For example, in some embodiments, patient support apparatus 20 is adapted to communicatively couple to a patient pendant that includes a control panel on it. In such embodiments, the patient pendant communicates with patient support apparatus 20, either via a cable or a wireless connection. Controller 60 may be configured to automatically lock out controls on the patient pendant, either in addition to, or in lieu of, the controls on one or more patient control panels 44*c* that are built into patient support apparatus 20.

In some embodiments of patient support apparatus 20, controller 60 is configured to allow a user to customize one or more aspects of the auto-locking function described herein. For example, in some embodiments, controller 60 is configured to allow a user to specify which controls on patient control panel 44*c* are to be locked out in response to a triggering event. Additionally, or alternatively, controller 60 may be configured to allow a user to customize what events controller 60 will treat as a triggering event for purposes of automatically applying one or more lockouts. Still further, controller 60 may be configured to allow a user to combine specific controls that are automatically locked out with specific triggering events such that, for example, a first control on patient control panels 44*c* is locked out in response to first and second triggering events, while a second control on patient control panels 44*c* is locked out in response to a third triggering event that is different from the first and second triggering events. In yet another embodiment, controller 60 may be configured to allow a caregiver to customize which control panels 44 have one or more controls automatically locked out, and the selection of these control panels 44 by the caregiver may be different for different controls 50 and/or for different triggering events. Still other combinations of customized triggering events, auto-locked controls 50, and/or control panels 44 may also be implemented.

Figure 9:
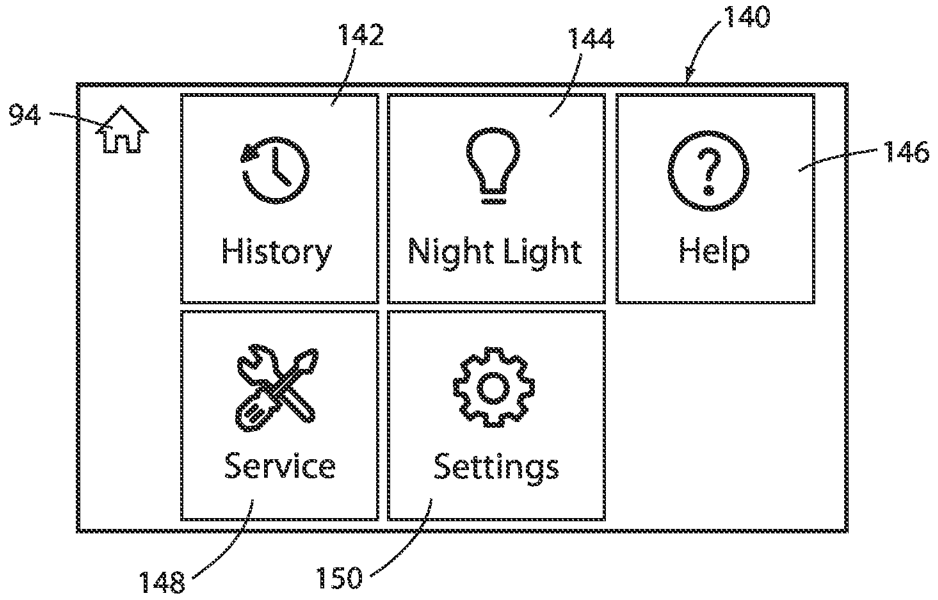
FIG. 9 is an illustrative menu screen that may be displayed on the display of the patient support apparatus.
Figure 10:
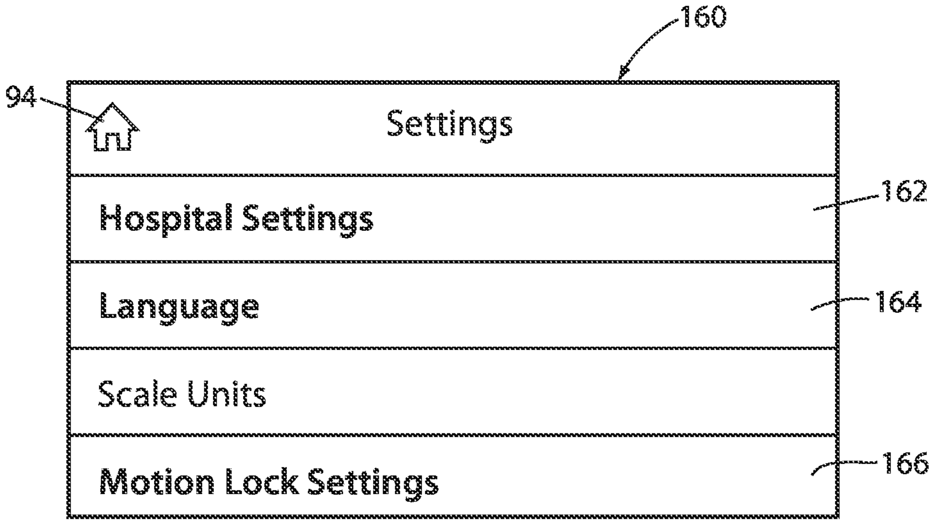
FIG. 10 is an illustrative settings screen that may be displayed on the display of the patient support apparatus.
Figure 11:
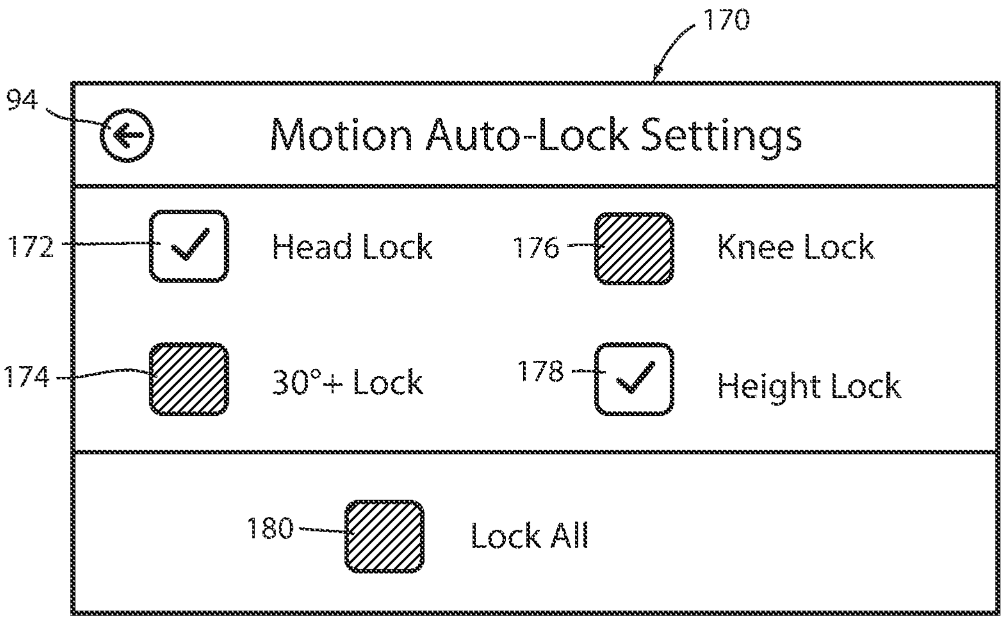
FIG. 11 is an illustrative auto-motion lock control screen that may be displayed on the display of the patient support apparatus.

FIGS. 9-11 illustrate one manner in which patient support apparatus 20 may be constructed in order to allow a user to select what controls 50 on patient control panels 44*c* are to be automatically locked out in response to a triggering event. FIG. 9 illustrates one example of a menu screen 140 that may be displayed on display 52 in response to a user pressing on menu control 50*f* (FIG. 2). Alternatively, or additionally, controller 60 may be configured to allow a user to navigate to menu screen 140 in other manners. However reached, menu screen 140 allows a user to view and/or change a variety of different parameters related to patient support apparatus 20.

As shown in the example of FIG. 9, menu screen 140 includes a home control 94, a history selector 142, a night light selector 144, a help selector 146, a service selector 148, and a settings selector 150. Controller 60 is configured to display history information regarding patient support apparatus 20 in response to a caregiver selecting history selector 142. Controller 60 is configured to display a night light control screen for controlling a night light (not shown) on patient support apparatus 20 in response to a caregiver selecting night light selector 144. Controller 60 is configured to display additional information about the use of patient support apparatus 20 in response to a caregiver selecting help selector 146. Controller 60 is configured to display a service history and/or other service information regarding patient support apparatus 20 in response to a caregiver selecting service selector 148.

Controller 60, in some embodiments, is configured to display a settings screen 160 (FIG. 10) in response to a user selecting the settings selector 150 of menu screen 140 (FIG. 8). Alternatively, or additionally, controller 60 may be configured to allow a user to navigate to setting screen 160 in other manners. However reached, settings screen 160 allows a user to view and/or change a variety of different settings for patient support apparatus 20, such as, but not limited to, the auto-locking function carried out by controller 60 and described herein.

Settings screen 160 includes a hospital settings selector 162, a language selector 164, and a motion lock settings selector 165. Controller 60 is configured to display settings related to the particular healthcare facility, or unit of the healthcare facility, in response to the caregiver selecting hospital settings selector 162. Controller 60 is configured to display language settings—which may allow the user to change the language of the information displayed on display 52—in response to the caregiver selecting language selector 164. Controller 60 is configured to display an auto-motion lock control screen in response to the caregiver selecting motion lock selector 166.

One example of an auto-motion lock control screen that may be displayed by controller 60 on display 52 in response to a user selecting motion lock selector 166 (FIG. 10) is the auto-motion lock control screen 170 of FIG. 11. Auto-motion lock control screen 170 includes a home selector 94, a head lock selector 172, a thirty degree lock selector 174, a knee lock selector 176, a height lock selector 178, and a select all selector 180. Screen 170 is adapted to allow a user to select what controls on patient control panel 44*c* are to be locked out automatically in response to one or more triggering events. If the caregiver selects head lock selector 172, controller 60 is configured to automatically lock out the Fowler controls 50 (e.g. controls 50*z* and 50*aa*) on patient control panels 44*c* in response to the triggering event. If the caregiver selects thirty degree lock selector 174, controller 60 is configured to lock out Fowler lowering control (e.g. control 50*aa*) when the angle of the Fowler section reaches 30 degrees. In other words, if the caregiver selects thirty degree lock selector 174, controller 60 is configured to prevent the patient from using Fowler control 50*aa* to lower the Fowler section of patient support apparatus 20 to an angular orientation of less than thirty degrees. Thirty degree lock selector 174 is therefore useful in situations where the caregiver does not want the patient to lie flat, or at angles where the Fowler section is less than 30 degrees.

Controller 60 is further configured to automatically lock out the knee controls (e.g. controls 50*x* and 50*y*) on patient control panels 44*c* in response to a triggering event if the caregiver has selected knee lockout selector 176 (FIG. 11). If the caregiver selects height lockout selector 178 (FIG. 11), controller 60 is configured to automatically lock out the height controls (e.g. controls 50*bb* and 50*cc*) on patient control panel 44*c* in response to the triggering event. And if the caregiver selects the lock all selector 180 on screen 170, controller 60 is configured to automatically implement all of the lockouts of selectors 172, 174, 176, and 178 shown in FIG. 11 in response to the triggering event.

It will be understood by those skilled in the art that, although FIG. 11 only illustrates four automatic lockouts that the caregiver can select, controller 60 may be configured in some embodiments to offer additional, or different, lock outs selections on screen 170 so that the automatic lock out functions can be customized in different manners. Further, although not shown in the drawings, in some embodiments, controller 60 is configured to provide a triggering control screen similar that lists a plurality of triggering event selectors and allows the caregiver to select which event or events will trigger the automatic lock out functions. Additional controls may also be provided that allow the caregiver to select which triggering events are associated with individual controls 50 on control panels 44*c*, thus allowing a caregiver to customize the automatic lockout controls such that, for example, a first control on patient control panels 44*c* is automatically locked out in response to either of triggering events A or B, while a second control on patient control panels 44*c* is automatically locked out in response to a triggering event C.

It will also be understood that, although FIG. 11 only illustrates a single lockout selector for a particular patient control (e.g. a single lockout selector 176 for the knee controls 50*x* and 50*y*), lockout control screen 170 may be modified to have two different selectors to match the two different directions in which the components of patient support apparatus 20 may be moved. For example, in some embodiments, lockout control screen 170 may have a first knee lockout selector 176 that corresponds to the control (50*x*) for raising the knee section of the support deck 30, and a second knee lockout selector 176 that corresponds to the control (50*y*) for lowering the knee section of the support deck 30. That is, instead of locking out the motion controls for both directions of movement, lockout control screen 170 may be modified to allow the caregiver to selectively lock out only certain directions of movement (e.g. movement that lowers litter frame 28 (e.g. control 50*cc*) might be permitted while movement that raises litter frame 28 (e.g. control 50*bb*) might be locked out). Still other variations to lockout control screen 170 and the functions associated with it may be made.

FIGS. 12 and 13 illustrate different manners in patient support apparatus 20 may display indications for automatic lockouts versus manual lockouts. More specifically, FIG. 12 illustrates a manual lockout control screen 190 that is displayable on display 52 in response to a user pressing on lockout control 50*e* (FIG. 2). Controller 60 may also, or alternatively, be configured to allow a caregiver to navigate to manual lockout control screen 190 in still other manners. Manual lockout control screen 190 includes a manual knee lockout selector 192, a manual Fowler lockout selector 194, and a manual height lockout selector 196. Manual lockout control screen 190 also includes a lock all selector 198 and a height control icon 200 having a vertical arrow icon 202 and a bed icon 204. If a caregiver presses on knee lockout selector 192, controller 60 is configured to manually lock out the knee controls 50*x* and 50*y* on patient control panels 44*c*. If a caregiver presses on Fowler lockout selector 194, controller 60 is configured to manually lock out the Fowler controls 50*z* and 50*aa* on patient control panels 44*c*. If the caregiver presses on height lockout selector 196, controller 60 is configured to manually lock out height controls 50*bb* and 50*cc* on patient control panels 44*c*. If the caregiver presses on lock all selector 198, controller 60 is configured to manually lock out the knee controls 50*x* and 50*y*, the Fowler controls 50*z* and 50*aa*, and the height controls 50*bb* and 50*cc* on patient control panels 44*c*.

In some embodiments, all of selectors 192, 194, 196, and 198 are toggle selectors such that, when repeatedly pressed, they alternate between turning on the corresponding manual lock outs and turning off the manual lock outs. Thus, for example, when the caregiver presses control 192 a first time, controller 60 manually locks out the knee controls on patient control panels 44*c*, and when the caregiver presses control 192 a second time, controller 60 manually unlocks the knee controls on patient control panels 44*c*. It will be understood that the manual lock outs differ from the automatic lockouts previously discussed in that the manual lock outs do not include a triggering event. That is, the manual lock outs take place immediately following caregiver turning them on, such as via selectors 192-198. Similarly, they are immediately unlocked upon the caregiver manually turning them off, such as via selectors 192-198.

Controller 60, in some embodiments, is adapted to display selectors 192-196 in a different manner when they are in the locked out state and when they are in the unlocked state. In the example shown in FIG. 12, controller 60 displays the height lockout selector 196 in a different manner than the selectors 192 and 194 because the height selector 196 is currently active. In some embodiments, this different manner of displaying the selectors 192-196 involves changing the color of the circle that surrounds the periphery of the selector 192-196, as well as changing the color of the lock symbol that appears inside the circle. Thus, in the example shown in FIG. 12, the lock symbol and circle of height selector 196 may be displayed in a first color (e.g. amber) to signify that the height controls 50*bb* and 50*cc* on the patient control panels 44*c* are locked out, while the lock symbols and circles of selectors 192 and 194 may be displayed in a second color (e.g. white) to signify that the corresponding knee and Fowler controls are not currently manually locked out.

In addition to changing the color of the circle and lock symbols to indicate that a particular lock out has been manually activated, controller 60 may be configured to change the color of one or more aspects of the icon that appears above the circles of selectors 192-196. Thus, in some embodiments, controller 60 is adapted to change the color of height control icon 200 when the height control lockout has been manually activated. Height control icon 200 includes an arrow icon 202 and a bed icon. In some embodiments, controller 60 changes the color of the arrow icon 202 (such as to an amber color) when the height control lockout is manually activated. This color change may be the same color change that controller 60 makes to the circle and lock symbol of selector 196.

In some embodiments, controller 60 is configured to provide a different indication for when an automatic lock out is activated, as opposed to a manual lock out. FIG. 13 illustrates lockout control screen 190 when the height lockout selector 196 has been automatically activated by controller 60 in response to a triggering event. In this particular example, controller 60 is configured to add the letter "A" to the lock icon to indicate that the height controls on the patient control panels 44*c* have been automatically locked out, as opposed to being manually locked out. Controller 60 may also distinguish this automatic lock out from the manual lock out by keeping the lock symbol and the circle around the lock symbol the same color as they appear when there is no manual lock out (e.g. white). Controller 60 may, however, change the color of the arrow icon 202 to a color (e.g. amber) that is the same as its color when the height controls are manually locked out. It will of course be understood that controller 60 may be configured to provide different indications on lockout control screen 190 than those shown in FIGS. 12 and 13 for distinguishing between manually activated lock outs and automatically implemented lock outs. In some embodiments, the different indicators for manual and automatic lockouts are only shown on one or more of the caregiver control panels 44*a* and/or 44*b*. For the patient control panels 44*c*, controller 60 may change the motion controls that are locked out in the same manner, regardless of whether they have been manually locked out or automatically locked out. The change is intended to provide an indication to the patient that the controls have been locked out so that the patient will understand that their disablement is intentional, and not the result of a malfunction. In some embodiments, controller 60 may not make any changes to the patient control panels 44*c* to indicate whether a control is locked out or not.

In some embodiments, controller 60 is configured to display a timer prior to automatically putting one or more of the controls on patient control panels 44*c* into a locked state. One example of such a timer is shown in FIGS. 14A-14D. Other types of timers may also or alternatively be displayed. The specific timer shown in FIGS. 14A-14D is for locking out the height controls (50*bb* and 50*cc*) on patient control panels 44*c*. In response to a triggering event, controller 60 is configured to first display the height control icon 200 and height selector 196 in the manner shown in FIG. 14A. In this state, a highlighted circle 210 completely surrounds height lock out selector 196. As time progresses, controller 60 automatically shortens the length of highlighted circle 210. Thus, in FIG. 14B, highlighted circle 210 only partially surrounds the lock icon. In FIG. 14C, the highlighted circle 210 surrounds the lock icon even less than in FIG. 14B. In FIG. 14D, the highlighted circle 210 is almost completely gone. Controller 60 is configured to continue to reduce the size of highlighted circle 210 until it is completely gone, at which point it automatically implements the corresponding lockouts. The gradual reduction of the size of highlighted circle 210 therefore provides a visual indication to the caregiver of how much time remains until the automatic lock out is implemented. In different embodiments, the amount of time it takes for controller 60 to reduce highlighted circle 210 so that it completely disappears may vary.

In some embodiments, controller 60 is configured to display a timer prior to automatically implementing a particular lock out for only certain triggering events and/or for only certain controls that are locked out. That is, in some embodiments, controller 60 displays a timer only for certain controls on patient control panels 44*c* that are automatically locked out and/or in response to only certain triggering events. The selection of which controls to display the timer for, and/or the selection of which triggering events to display the timer for, may be customized by the caregiver in some embodiments of patient support apparatus 20.

It will be understood that, although the foregoing discussion has described a plurality of controls that are automatically locked out on one or more control panels and a plurality of different triggering conditions for the lock outs of these controls, patient support apparatus 20 may be configured in different embodiments to implement only some of these automatic lock outs and/or triggering events. That is, different embodiments of patient support apparatus 20 may be implemented that use fewer (or only a single) triggering event, and/or that only automatically lock out a single control on patient control panels 44*c* (e.g. only height raising control 50*bb*). It will also be understood that, although patient support apparatus 20 has been described herein as having both manual and automatic lock outs, it may be modified in some embodiments to include only automatic lock outs and not include any manual lock outs.

In some embodiments, patient support apparatus server 76 may be configured to share the lock out status of patient support apparatus 20 with one more electronic devices (e.g. smart phones, tablet computers, laptop computers, and/or other devices). Such sharing of lock out information may be accomplished, in some embodiments, by including this information in a caregiver assistance software application that is executed on these electronic devices. One example of such a caregiver assistance software application into which the lock out status information may be incorporated is the caregiver assistance application 124 disclosed in commonly assigned U.S. patent application Ser. No. 62/868,947 filed Jun. 30, 2019, by inventors Thomas Durlach et al. and entitled CAREGIVER ASSISTANCE SYSTEM, the complete disclosure of which is incorporated herein by reference.

In some embodiments, controller 60 may be configured to automatically implement different motion limits for movement of one or more components of patient support apparatus 20 depending upon whether the motion was initiated by one of the caregiver control panels 44*a, b* or by one of the patient control panels 44*c*. That is, in some embodiments, controller 60 limits how far one or more actuators 26, 64, and/or 66 are able to move a component in a particular direction to a first limit if the actuator was activated by a control from one of the caregiver control panels 44*a* and/or 44*b*, and limits how far that same actuator may be driven in the same particular direction to a second and different limit if the actuator was activated by a control from one of the patient control panels 44*c*. In this manner, the patient is restricted from moving one or more components of patient support apparatus 20 with the same degree of freedom as the caregiver.

For example, in some embodiments, when a patient activates the height up control 50*bb* on patient control panel 44*c*, controller 60 is configured to automatically stop upward movement of the litter frame 28 (via lifts 26) when the litter frame 28 reaches a first height that is less than the maximum height to which litter frame 28 can be lifted by lifts 26. In such embodiments, when a caregiver activates the height up control 50*p* on caregiver control panel 44*b* (or a similar height up control on caregiver control panel 44*a*), controller 60 is configured to automatically stop upward movement of the litter frame 28 (via lifts 26) when the litter frame 28 reaches a second height that is higher than the first height (and which may or may not be less than the maximum height to which litter frame 28 can be lifted by lifts 26). As a result, a patient is only able to raise the height of litter frame 28 to a height that is less than the height to which the caregiver is able to raise the height of litter frame 28. Or, stated alternatively, a caregiver using height up control 50*p* is able to raise litter frame 28 to a higher height than a patient using height up control 50*bb*.

In some embodiments, patient support apparatus 20 is configurable by a user to allow the user to select what motion controls on patient control panels 44*c* will have different limits than the corresponding controls on caregiver control panels 44*a, b*. For example, if a caregiver or other authorized healthcare administrator wants to be able to lower litter frame 28 to a very low height, but to prevent the patient from lowering litter frame 28 to that same low height, the user can utilize control panel 44*a* to navigate to a screen that enables the user to set a first height limit for the height down controls 50*q* on caregiver control panels 44*b* (and any similar height down controls of control panel 44*a*) and set a second and different height limit for the down controls 50*cc* on patient control panels 44*c*. Patient support apparatus 20 may be configured to allow the user to use the same screen, or a similar screen, to set a first limit for any one or more of the motion controls on patient control panel 44*c* that is different from a corresponding limit for the motion controls on caregiver control panel 44*b* and/or 44*a*. These motion controls include any motion controls that are common to the patient control panels 44*a* and the caregiver control panels 44*a, b*. As a result, patient support apparatus 20 is, in some embodiments, configurable by a user to set motion limits for any one or more of motion controls 50*x* through 50*cc* that are different than the corresponding motion limits for motion controls 50*l* through 50*cc*.

Additionally, in some embodiments, patient control panels 44*c* may be modified from what is shown in FIG. 5 to include one or more additional motion controls that are found on caregiver control panel 44*b*, such as, but not limited to, a flat position control comparable to flat position control 50*g* of caregiver control panel 44*b*. When patient controls panels 44*c* are modified to include additional motion controls having corresponding counterparts on caregiver control panels 44*b* and/or 44*a*, controller 60 may be configured to allow the user to set different motion limits for patient control panels 44*c* versus the caregiver control panels 44*a* and 44*b*. Similarly, in some embodiments, caregiver control panels 44*b* may be modified from what is shown in FIG. 4 to include one or more additional controls that are found on patient control panels 44*a*, such as, but not limited to, a chair position control comparable to chair position control 50*dd* and/or an egress control comparable to egress control 50*u*. When caregiver control panels 44*b* and/or 44*a* are modified to include additional motion controls having corresponding counterparts on patient control panels 44*a*, controller 60 may be configured to allow the user to set different motion limits for caregiver control panels 44*a, b* versus the patient control panels 44*c*. Still other motion controls may be added to the caregiver and patient controls panels and patient support apparatus 20 may be configurable by a user to have different motion limits for the added controls, depending upon whether the motion is activated using a patient control panel 44*c* versus a caregiver control panel 44*a* and/or 44*b*.

In some embodiments, the patient support apparatus 20 is further configurable by a user to determine which control panels 44*a-c* will have different motion limits than other ones of the control panels 44*a-c*. Thus, for example, in some embodiments, patient support apparatus 20 may be configured by a user to have different motion limits for footboard caregiver control 44*a* than the motion limits for the siderail control panels 44*b* and 44*c*. This may be useful in preventing the patient from moving patient support apparatus 20 to an undesired configuration by preventing the patient from simply reaching over one of the siderails 36 to access one of the siderail caregiver control panels 44*b*. In other words, in some embodiments, instead of setting motion limits for patient control panels 44*c* that are different from caregiver control panels 44*a* and/or *b*, patient support apparatus 20 is configurable to allow the user to set motion limits for siderail control panels 44*b* and 44*c* that are different from the motion limits for footboard control panel 44*a*. Still other variations are possible.

In some embodiments, in order to prevent a patient from using footboard control panel 44*a*, controller 60 is configured to lock out access to footboard control panel 44*a* unless an authorized user enters a passcode into control panel 44*a*. In some of such embodiments, controller 60 is configured to automatically disable footboard control panel 44*a* after a certain amount of time passes without usage. In such embodiments, controller 60 may be configured to continue to disable control panel 44*a* until a caregiver enters a passcode into footboard control panel 44*a*. Once the correct code is entered, controller 60 may be configured to enable control panel 44*a*. The enablement may continue for as long as the control panel 44 is used with sufficient frequency and/or for a predetermined amount of time without usage. Alternatively, or additionally, controller 60 may include a control that, when activated by the caregiver, disables the control panel 44*a* until the passcode is re-entered.

Figure 15:
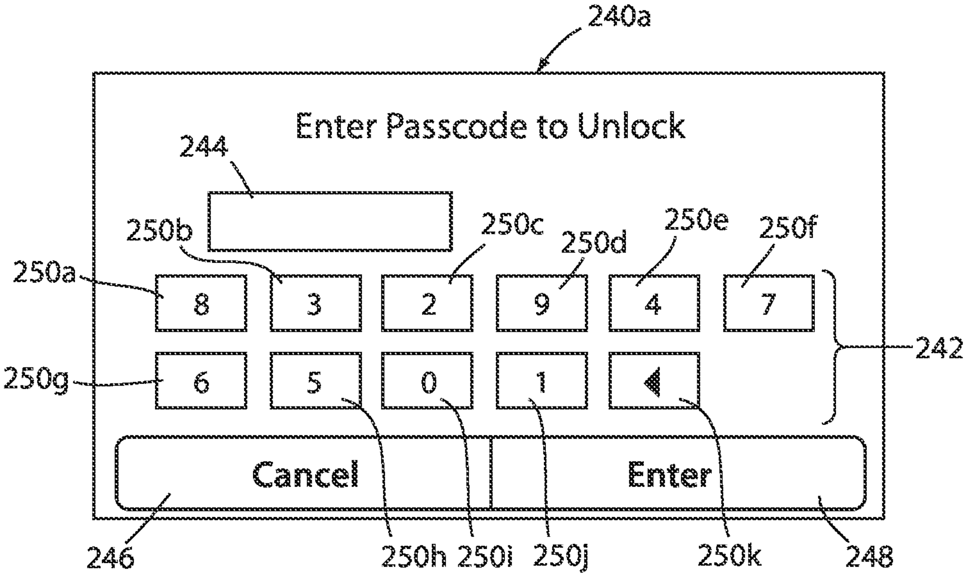
FIG. 15 is a first illustrative passcode screen that may be displayed on the display of the patient support apparatus.
Figure 16:
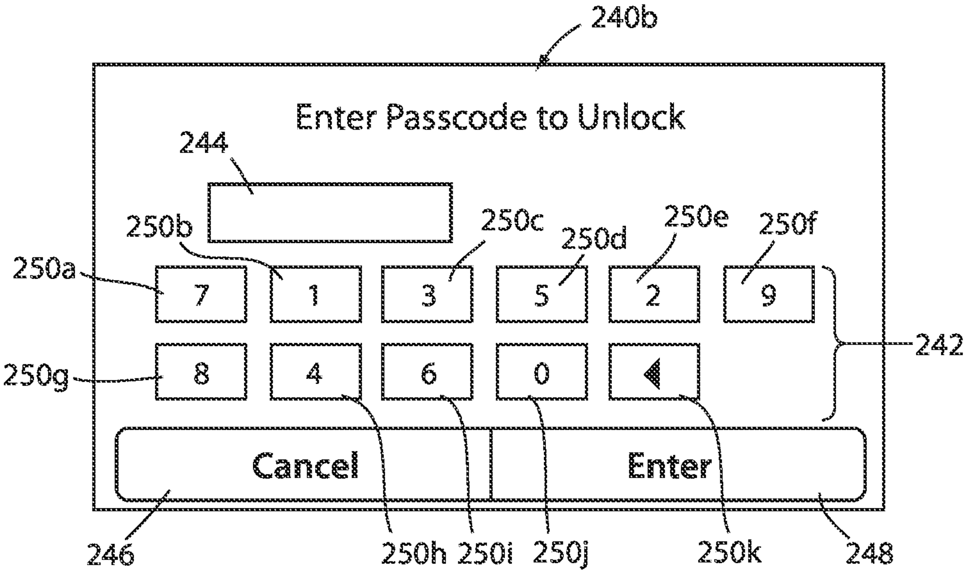
FIG. 16 is a second illustrative passcode screen that may be displayed on the display of the patient support apparatus.

Regardless of whether manually or automatically disabled, controller 60 is configured in some embodiments to require the caregiver to enter a passcode before controller 60 enables the use of control panel 44*a*. FIGS. 15 and 16 illustrate two examples of a passcode screen 240*a* and 240*b* that may be displayed by controller 60 on control panel 44*a*. Passcode screens 240*a* and 250*b* both include a keypad 242, a code entry field 244, a cancel control 246, an enter control 248, and a plurality of keys 250*a-k*. In order for a user to enter a passcode, the caregiver presses on a series of the keys 250*a-j*. For each key 250*a-j* that is pressed by the caregiver, controller 60 enters the number corresponding to the pressed key 250*a-j* into code entry field 244. If the user presses on an inadvertent key, the user can erase the numeric entry by pressing on the backspace key 250*k*, which, for each press of key 250*k*, erases the most recently entered number in field 244. Once the desired passcode has been entered into field 244, the user presses on enter control 248 and controller 60 checks to see if the code entered in field 244 matches the code stored in the memory of patient support apparatus 20. If they match, controller 60 enables control panel 44*a*, such as by displaying screen 140 (or another screen) on display 52. If they do not match, controller 60 continues to disable the functionality of control panel 44*a*, thereby preventing unauthorized usage of the control panel 44*a* (such as by the patient). If the caregiver presses the cancel control 246, controller 60 continues to disable usage of control panel 44*a*.

In order to help prevent a patient from deducing the correct passcode by watching the movement patterns of the caregiver's hand and/or fingers while he or she enters the correct passcode (and/or to help prevent the patient from guessing the passcode through a fingerprint smudge analysis), controller 60 is configured to scramble the numbers assigned to keys 250*a-j* each time it displays a passcode screen 240. By doing this, each time a caregiver enters the correct passcode, he or she will utilize a different hand movement pattern (and press different areas on touchscreen display 52), thereby making it more difficult for a patient who is watching the caregiver (but doesn't see screen 240) to determine what the correct passcode is. It can therefore be seen that screens 240*a* and 240*b* of FIGS. 15 and 16 are merely two examples of the passcode screens that controller 60 may display. As noted, each time controller 60 displays a passcode screen 240, it is configured to scramble the numbers that correspond to keys 250*a-j*.

This scrambling is evident from a comparison of FIGS. 15 and 16. In FIG. 15, key 250*a* corresponds to the number "8," key 250*b* corresponds to the number "3," key 250*c* corresponds to the number "2," key 250*d* corresponds to the number "9," key 250*e* corresponds to the number "4," key 250*f* corresponds to the number "7," key 250*g* corresponds to the number "6," key 250*h* corresponds to the number "5," key 250*i* corresponds to the number "0," and key 250*j* corresponds to the number "1." In FIG. 16, controller 60 has changed this correspondence. Specifically, in FIG. 16, key 250*a* corresponds to the number "7," key 250*b* corresponds to the number "1," key 250*c* corresponds to the number "3," key 250*d* corresponds to the number "5," key 250*e* corresponds to the number "2," key 250*f* corresponds to the number "9," key 250*g* corresponds to the number "8," key 250*h* corresponds to the number "4," key 250*i* corresponds to the number "6," and key 250*j* corresponds to the number "0." In some embodiments, controller 60 may also scramble what key 250*a-k* corresponds to the backspace key 250*k*.

Controller 60 is configured, in some embodiments, to use a random number generator and/or a pseudo-random number generator to determine which key 250*a-j* corresponds to which of numbers 0 through 9 for a particular instance of passcode screen 240. That is, each time controller 60 displays a passcode screen 240, it is configured to randomly assign the numbers 0 through 9 to each of the keys 250*a-j*. In this manner, each time a caregiver is presented with a passcode screen 240, the particular assignment of keys 250*a-j* to particular numbers 0 through 9 will change. The passcode screens 240*a* and 240*b* of FIGS. 15 and 16 are therefore merely two examples of a large number of variations of the passcode screens 240 that controller 60 may dynamically generate.

As a consequence of the changing assignment of numbers to keys 250*a-j*, when the caregiver uses the keys 250*a-j* to enter the correct passcode, the locations on display 52 that the caregiver touches when entering the passcode will change, thereby making it more difficult for a patient who is watching the caregiver's hands while entering the passcode to guess the correct passcode. This helps prevent the patient from controlling patient support apparatus 20 in a manner that might not be desired by the healthcare facility.

It will be understood that, in those embodiments of patient support apparatus 20 that include the aforementioned keypad scrambling function, such embodiments may be configured to allow authorized personnel to turn on and turn off this scrambling function. The ability to turn on/off this function may be accomplished by navigating to a settings screen, or the like, using footboard control panel 44*a*, wherein one of the settings includes a user selection of having keypad 242 scrambled or not scrambled. In some embodiments, the settings screen may also allow the user to shut off completely the keypad function 242, thereby allowing all users to have access to all of the control panels 44*a-c* without first requiring that a passcode is entered.

It will be understood that a number of variations may be made to the passcode screens 240*a* and 240*b*. For example, in addition to, or in lieu of, changing the numbers assigned to each key 250*a-j*, controller 60 may be configured to change the overall location of keypad 242 on display 52 so that each time a passcode screen 240 is displayed, the location of keypad 242 changes. Alternatively, or additionally, controller 60 may be configured to change the location of passcode entry field 244, cancel control 246, and/or enter control 248 each time it displays a passcode screen 240. Still other variations are possible.

In some embodiments, controller 60 is configured to lock out the functioning of not only footboard control panel 44*a* until the correct passcode is entered, but to also lock out one or more (or all) of the other control panels 44*b* and 44*c* until the user enters the correct passcode, and/or to lock out selected controls on one or more (or all) of the other control panels 44*b* and 44*c*. That is, in some embodiments, for example, controller 60 is configured to disable the functionality of all of the motion controls on control panels 44*a*, 44*b*, and 44*c* after a predetermined time period elapses without usage (or a caregiver manually disables these controls). In such embodiments, controller 60 continues to disable the motion controls on all of the control panels 44*a*, 44*b*, and 44*c* until a caregiver enters the correct passcode into passcode field 244. This lockout of the motion controls on all of the control panels 44*a*, 44*b*, and 44*c* may be especially useful when patient support apparatus 20 is used with a patient who may be suffering from a behavioral health issue.

By locking out the motion controls on all of the control panels 44a, 44b, and 44c, controller 60 helps prevent a patient from using patient support apparatus 20 to harm themselves. Further, by randomly scrambling the numbers of keypad 242 on screens 240, controller 60 is configured to help prevent the patient from determining the correct passcode, and thereby helps prevent the patient from moving any of the components of patient support apparatus 20 when the caregiver is not present. In such embodiments, controller 60 may be configured to allow the patient to utilize other controls on patient control panels 44c while the motion controls are locked out, such as a nurse call control (not shown), a television control, or any other controls that are unrelated to movement of patient support apparatus and/or patient safety.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:

a base;

a plurality of lifts;

a frame supported on the lifts, wherein the lifts are adapted to change a height of the frame;

a support surface supported on the frame and adapted to support a patient thereon;

a caregiver control panel including a lockout control adapted to be activated by a caregiver;

a patient control panel including a first control adapted to be activated by the patient, the first control having a locked state and an unlocked state, the first control adapted to move a component of the patient support apparatus when activated while in the unlocked state, the first control adapted to not move the component of the patient support apparatus when activated while in the locked state; and a controller in communication with the patient control panel and the caregiver control panel, the controller adapted to change the first control to the locked state in response to the lockout control being manually activated, to also change the first control to the locked state in response to detecting a triggering event, to detect cessation of the triggering event, and in response to detecting the cessation of the triggering event, to perform at least one of the following:

(a) return the first control to the unlocked state if the first control was in the unlocked state prior to detection of the triggering event, or (b) leave the first control in the locked state if the first control had been activated into the locked state by manual activation of the lockout control prior to detection of the triggering event.

2. The patient support apparatus of claim 1 wherein the first control is a height control adapted to raise a height of the frame when the height control is activated and the lockout control is not activated.

3. The patient support apparatus of claim 1 wherein the caregiver control panel is adapted to enter a sleep mode after a predetermined time period elapses without the caregiver using the caregiver control panel, and wherein the triggering event is the caregiver control panel being in the sleep mode.

4. The patient support apparatus of claim 1 wherein the controller is further adapted to receive a fall risk score of the patient, and wherein the triggering event is the fall risk score exceeding a threshold level.

5. The patient support apparatus of claim 1 further comprising an exit detection system adapted to be armed and disarmed and to operate with a plurality of different sensitivity levels when armed, the exit detection system adapted to issue an alert when the exit detection system is armed and a patient exits from the patient support apparatus, and wherein the triggering event is operating the exit detection system at a first one of the plurality of sensitivity levels but not at a second one of the plurality of sensitivity levels.

6. The patient support apparatus of claim 5 further comprising a second triggering event corresponding to the arming of the exit detection system at a third sensitivity level, and wherein the controller is further adapted to automatically lock out a second control different from the first control in response to detection of the second triggering event.

7. The patient support apparatus of claim 1 further comprising:

a plurality of wheels coupled to the base;

a brake adapted to selectively brake and unbrake at least one of the plurality of wheels;

a plurality of siderails adapted to be moved between raised and lowered positions; and a monitoring system adapted to be armed and disarmed and to monitor, when armed, a first state of the brake and a second state of the siderails and to issue an alert if any one of the first or second states changes to an undesired state, wherein the triggering event is the monitoring system being armed.

8. The patient support apparatus of claim 1 further comprising:

a scale system adapted to detect a weight of the patient; and a scale control positioned on the caregiver control panel;

wherein the controller is adapted to record the weight of the patient in response to activation of the scale control and the triggering event is recording the weight of the patient.

9. The patient support apparatus of claim 1 further comprising:

a scale system adapted to detect a weight of the patient; and a scale zeroing control positioned on the caregiver control panel;

wherein the controller is adapted to tare the scale system in response to activation of the scale zeroing control and the triggering event is the taring of the scale zeroing control.

10. The patient support apparatus of claim 1 further comprising:

a scale system adapted to detect a weight of the patient; and wherein the controller is further adapted to automatically and repetitively take weight readings from the scale system to determine if the patient is occupying the patient support apparatus or not, and wherein the triggering event is the patient not occupying the patient support apparatus.

11. A patient support apparatus comprising:
a base;
a plurality of lifts;
a frame supported on the lifts, wherein the lifts are adapted to change a height of the frame;
a support surface adapted to support a patient thereon;
a caregiver control panel including a lockout control adapted to be activated by a caregiver;
a patient control panel including a first control adapted to move of a component of the patient support apparatus when activated by the patient; and
a controller in communication with the patient control panel and the caregiver control panel, the controller adapted to automatically activate the lockout control and change the first control to a locked state in response to detecting a triggering event such that—when in the locked state activation of the first control does not move the component, the controller further adapted to perform the following:
to display a first lockout indication for the first control when the lockout control is manually activated by the caregiver,
to display a second lockout indication for the first control when the lockout control is automatically activated in response to the triggering event;
to display neither the first nor second lockout indication when the lockout control is not manually activated by the caregiver and the triggering event is absent, wherein the first lockout indication is different from the second lockout indication;
to detect cessation of the triggering event; and
in response to detecting the cessation of the triggering event, to perform at least one of the following:
(a) return the first control to an unlocked state if the first control was in the unlocked state prior to detection of the triggering event, or
(b) leave the first control in the locked state if the lockout control had been manually activated prior to detection of the triggering event.

12. The patient support apparatus of claim 11 wherein the first control includes a first icon and the first indication includes illuminating the first icon in a first manner and the second indication includes illuminating the first icon in a second manner different from the first manner.

13. The patient support apparatus of claim 12 wherein the second manner includes adding a letter "A" to the first icon.

14. The patient support apparatus of claim 11 wherein the first control is a height control adapted to raise a height of the frame when the height control is activated and the lockout control is not activated.

15. The patient support apparatus of claim 14 further comprising:
a scale system adapted to detect a weight of the patient; and
a scale control positioned on the caregiver control panel;
wherein the controller is adapted to record the weight of the patient in response to activation of the scale control and the triggering event is the activation of the scale control.

16. The patient support apparatus of claim 14 further comprising:
a scale system adapted to detect a weight of the patient; and
a scale zeroing control positioned on the caregiver control panel;
wherein the controller is adapted to tare the scale system in response to activation of the scale zeroing control and the triggering event is the activation of the scale zeroing control.

17. The patient support apparatus of claim 14 further comprising:
a scale system adapted to detect a weight of the patient; and
wherein the controller is further adapted to automatically and repetitively take weight readings from the scale system to determine if the patient is occupying the patient support apparatus or not, and wherein the triggering event is the patient not occupying the patient support apparatus.

18. The patient support apparatus of claim 14 wherein the lifts are adapted to tilt the frame, the support surface includes a section adapted to pivot, and the caregiver control panel includes a configuration control, wherein the controller is adapted to tilt the frame and pivot the section to a particular configuration when the configuration control is activated, and wherein the triggering event is the activation of the configuration control.

19. The patient support apparatus of claim 18 wherein the configuration control is adapted to tilt the frame and pivot the section to one of the following configurations: (a) a Trendelenburg configuration, (b) a reverse Trendelenburg configuration, (c) an examination configuration, or (d) a vascular configuration.

20. The patient support apparatus of claim 14 wherein the triggering event is a current height of the frame exceeding a threshold height.

* * * * *